US010117999B2

(12) United States Patent
Andersen

(10) Patent No.: US 10,117,999 B2
(45) Date of Patent: Nov. 6, 2018

(54) MEDICAL INJECTION SYSTEM WITH DOSE CAPTURING

(71) Applicant: Novo Nordisk A/S, Bagsvaerd (DK)

(72) Inventor: Jens Christian Andersen, Roskilde (DK)

(73) Assignee: Novo Nordisk A/S, Bagsvaerd (DK)

(*) Notice: Subject to any disclaimer, the term of this patent is extended or adjusted under 35 U.S.C. 154(b) by 634 days.

(21) Appl. No.: 14/759,558

(22) PCT Filed: Jan. 10, 2014

(86) PCT No.: PCT/EP2014/050363
§ 371 (c)(1),
(2) Date: Jul. 7, 2015

(87) PCT Pub. No.: WO2014/108494
PCT Pub. Date: Jul. 17, 2014

(65) Prior Publication Data
US 2015/0352288 A1 Dec. 10, 2015

Related U.S. Application Data

(60) Provisional application No. 61/752,024, filed on Jan. 14, 2013.

(30) Foreign Application Priority Data

Jan. 10, 2013 (EP) .................................... 13150893

(51) Int. Cl.
*A61M 5/315* (2006.01)
*A61M 5/20* (2006.01)
(Continued)

(52) U.S. Cl.
CPC .......... *A61M 5/31568* (2013.01); *A61M 5/20* (2013.01); *A61M 5/2033* (2013.01);
(Continued)

(58) Field of Classification Search
CPC ................ A61M 5/20; A61M 5/31528; A61M 5/31548; A61M 5/31568; A61M 5/2033;
(Continued)

(56) References Cited

U.S. PATENT DOCUMENTS 4,921,487 A 5/1990 Buffet et al.
4,959,056 A 9/1990 Dombrowski et al.
(Continued)

FOREIGN PATENT DOCUMENTS

DE 20309262 U1 8/2003
EP 2060284 A1 5/2009
(Continued)

*Primary Examiner* — Kevin C Sirmons
*Assistant Examiner* — Tiffany Legette-Thompson
(74) *Attorney, Agent, or Firm* — Wesley Nicolas

(57) ABSTRACT

The present invention relates to a medical injection system comprising an injection device (100) and a dose capturing unit (20). The injection device (100) incorporates expelling means (101) for setting and expelling a set dose amount of a drug from a reservoir. The expelling means (101) further comprises mechanical energy storage unit adapted to drive the expelling movement and a movable dosing member (350). In one form the dose capturing unit (20) is configured for being releasably attached to the injection device (100). The dose capturing unit (20) comprises a dose sensor (20*d*) configured to capture data relating to the movement of the dosing member (350) during dose expelling. When the dose capturing unit (20) is attached to the injection device (100), the systems forms a speed limiting means (F, M) to limit the speed of the dosing member (350) during dose expelling so that a force that counteracts the force exerted by the mechanical energy storage unit is generated.

13 Claims, 11 Drawing Sheets

(51) Int. Cl.
*A61M 5/24* (2006.01)
*A61M 5/31* (2006.01)
*G06F 19/00* (2018.01)

(52) U.S. Cl.
CPC .... *A61M 5/31528* (2013.01); *A61M 5/31548* (2013.01); *A61M 5/2053* (2013.01); *A61M 5/24* (2013.01); *A61M 2005/2086* (2013.01); *A61M 2005/2407* (2013.01); *A61M 2005/3126* (2013.01); *A61M 2005/31518* (2013.01); *A61M 2205/3365* (2013.01); *A61M 2205/3576* (2013.01); *A61M 2205/52* (2013.01); *A61M 2205/581* (2013.01); *G06F 19/3468* (2013.01)

(58) Field of Classification Search
CPC .. A61M 5/24; A61M 5/2053; A61M 2205/52; A61M 2205/3576; A61M 2205/581; A61M 2205/3365; A61M 2005/3126; A61M 2005/2407; A61M 2005/31518; A61M 2005/2086
See application file for complete search history.

(56) References Cited

U.S. PATENT DOCUMENTS

| | | | |
|---|---|---|---|
| 5,611,784 A | | 3/1997 | Barresi et al. |
| 2009/0318865 A1* | | 12/2009 | Moller .............. A61M 5/31553 604/135 |
| 2011/0077595 A1 | | 3/2011 | Eich et al. |
| 2011/0301534 A1* | | 12/2011 | Renz .................... A61M 5/2066 604/82 |
| 2011/0313349 A1* | | 12/2011 | Krulevitch .............. A61M 5/24 604/65 |

FOREIGN PATENT DOCUMENTS

| | | |
|---|---|---|
| JP | 2003180828 A | 7/2003 |
| WO | 2008037801 A1 | 4/2008 |
| WO | 2010/052275 A2 | 5/2010 |
| WO | 2010/098927 A1 | 9/2010 |
| WO | 2010/128493 A2 | 11/2010 |

\* cited by examiner

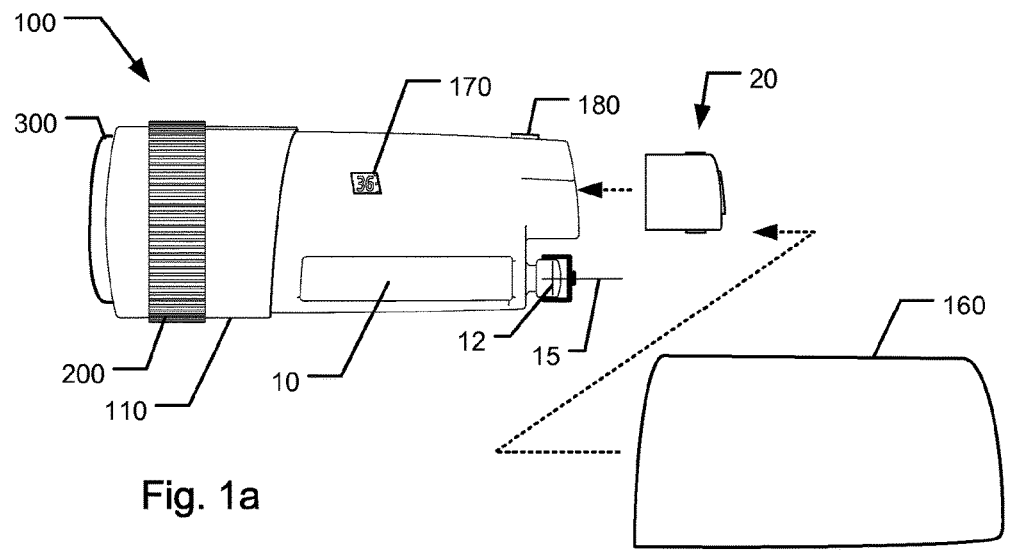
Fig. 1a
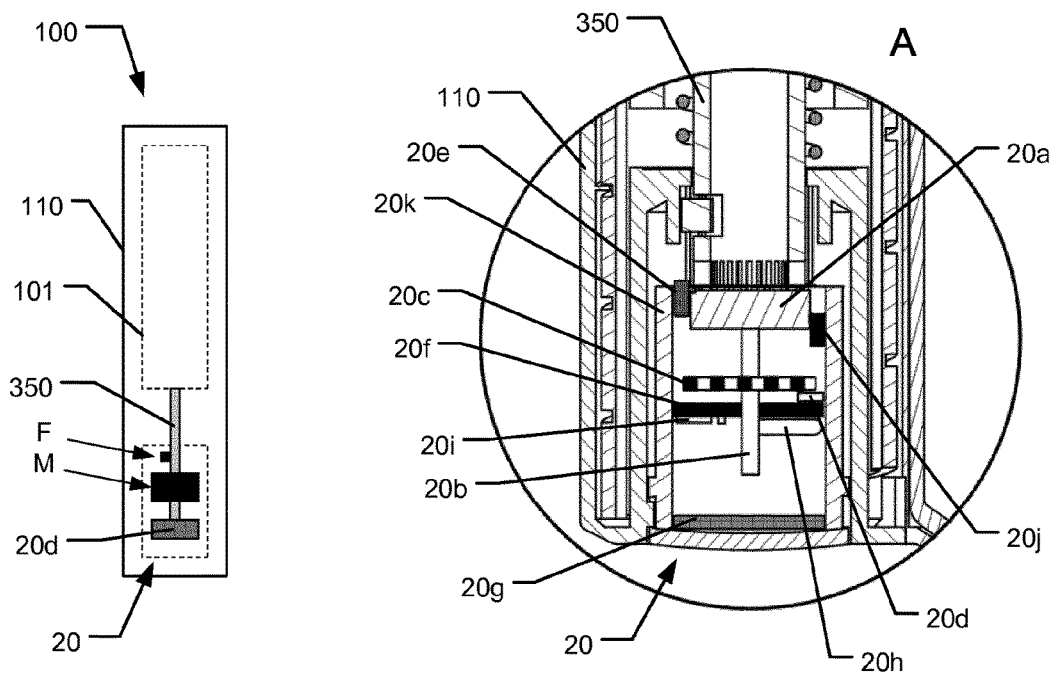
Fig. 1b
Fig. 2b

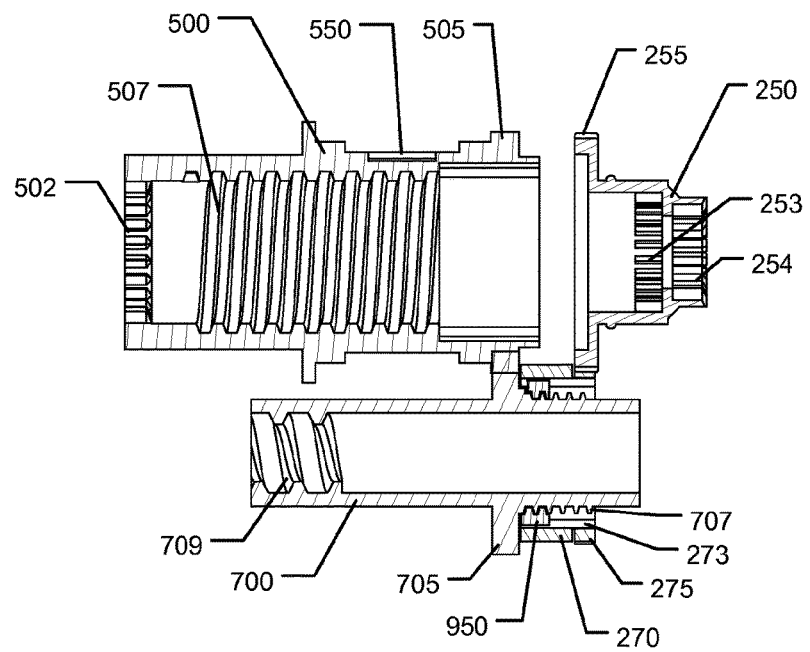
Fig. 5a
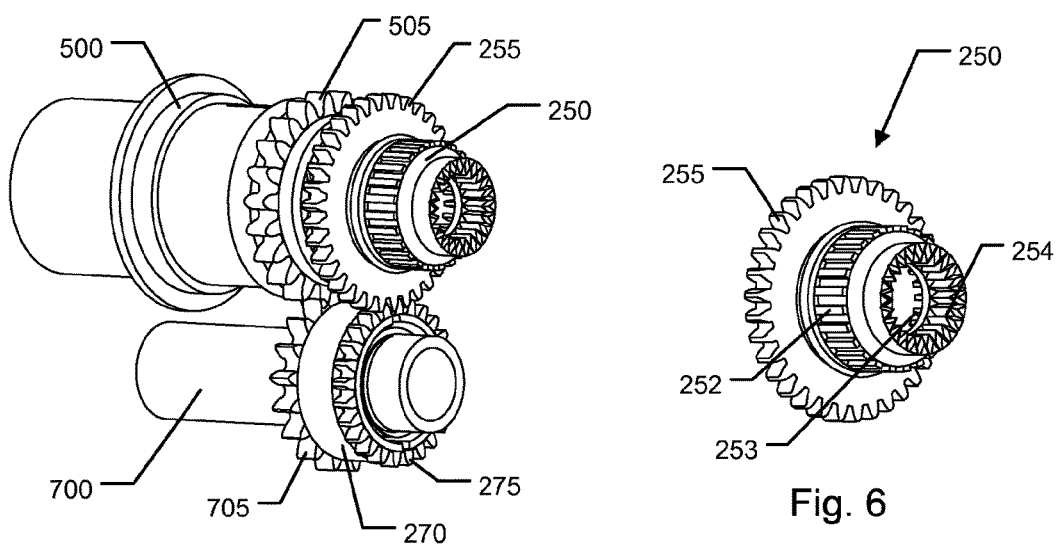
Fig. 5b
Fig. 6

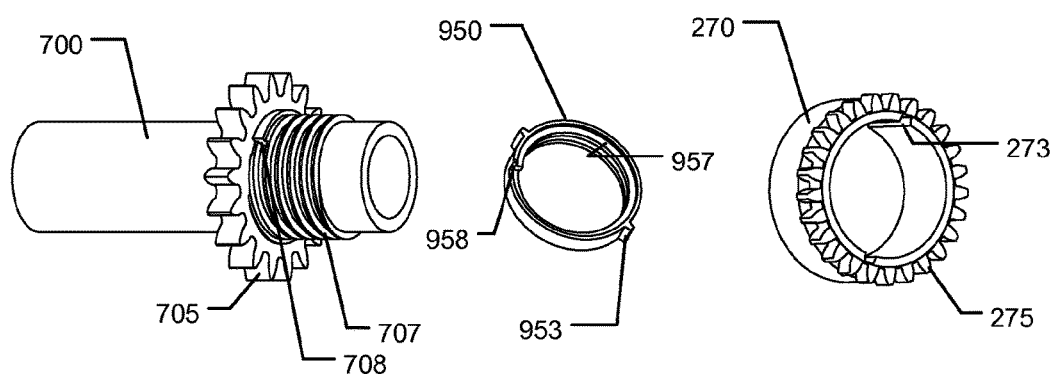
Fig. 7a   Fig. 7b   Fig. 7c
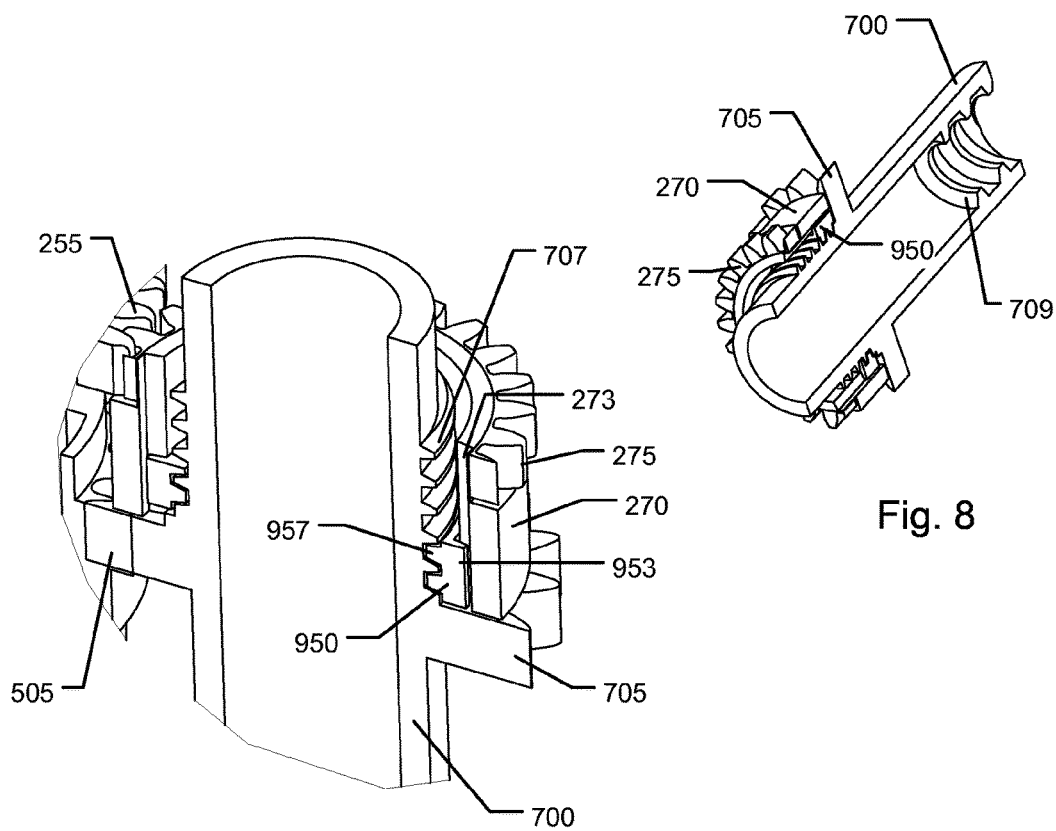
Fig. 8
Fig. 9

MEDICAL INJECTION SYSTEM WITH DOSE CAPTURING

CROSS-REFERENCE TO RELATED APPLICATIONS

This application is a 35 U.S.C. § 371 National Stage application of International Application PCT/EP2014/050363 (published as WO 2014/108494), filed Jan. 10, 2014, which claims priority to European Patent Application 13150893.9, filed Jan. 10, 2013; this application claims priority under 35 U.S.C. § 119 to U.S. Provisional Application 61/752,024; filed Jan. 14, 2013.

The present invention relates to a system for capturing drug delivery dose data. Especially, the invention addresses the issue of reliably monitoring dose expelling movements of an injection device that is driven by a mechanical energy storage unit.

BACKGROUND OF THE INVENTION

In the disclosure of the present invention reference is mostly made to the treatment of diabetes by delivery of insulin, however, this is only an exemplary use of the present invention.

Drug Injection devices have greatly improved the lives of patients who must self-administer drugs and biological agents. Drug Injection devices may take many forms, including simple disposable devices that are little more than an ampoule with an injection means or they may be durable devices adapted to be used with pre-filled cartridges. Regardless of their form and type, they have proven to be great aids in assisting patients to self-administer injectable drugs and biological agents. They also greatly assist care givers in administering injectable medicines to those incapable of performing self-injections.

Performing the necessary insulin injection at the right time and in the right size is essential for managing diabetes, i.e. compliance with the specified insulin regimen is important. In order to make it possible for medical personnel to determine the effectiveness of a prescribed dosage pattern, diabetes patients are encouraged to keep a log of the size and time of each injection. However, such logs are normally kept in handwritten notebooks, from the logged information may not be easily uploaded to a computer for data processing. Furthermore, as only events, which are noted by the patient, are logged, the note book system requires that the patient remembers to log each injection, if the logged information is to have any value in the treatment of the patient's disease. A missing or erroneous record in the log results in a misleading picture of the injection history and thus a misleading basis for the medical personnel's decision making with respect to future medication. Accordingly, it may be desirable to automate the logging of ejection information from medication delivery systems.

Though some injection devices integrate this monitoring/acquisition mechanism into the device itself, e.g. as disclosed in US 2009/0318865 and WO 2010/052275, most devices of today are without it. The most widely used devices are purely mechanical devices either durable or prefilled. The latter devices are to be discarded after being emptied and so inexpensive that it is not cost-effective to build-in electronic data acquisition functionality in the device it-self. Correspondingly, data acquisition/monitoring functionality have been proposed to be provided in a separate device to be put on or in the injection device, i.e. some kind of accessory e.g. an add-on module to the injection device.

For example, WO 2010/098927 discloses a medical module which is configured to be attached to a drug delivery pen, the module being adapted to detect and store selected and ejected dosages as well as other data. Further arrangements adapted to capture dose data are known from WO 2010/128493, EP 2 060 284, WO 2008/037801 and WO 2010/052275.

Injection devices that provide spring assisted drug expelling are becoming increasingly popular. However, for spring driven devices it is a challenging task to develop adequately performing electronic capturing systems that reliably monitor movements during expelling of a drug. Hence, expensive and more complex electronic dose capturing systems are required. US 2011/0301534 and U.S. Pat. No. 4,921,487 disclose spring driven delivery devices that include speed regulation means which are incorporated for ensuring a particular expelling drug rate. US 2011/077595 includes disclosure of various braking mechanisms for protecting the mechanism of the device against inadvertent operation that potentially would damage the mechanism.

Having regard to the above, it is an object of the present invention to provide systems and methods supporting simple and reliable yet cost- and energy-effective detection and storage of dose data related to use of a drug delivery device.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect of the invention a medical injection system is provided, comprising (a) an injection device configured for setting and expelling a set dose amount of a drug from a reservoir, and b) an electronically controlled dose capturing unit configured for being attached relative to the injection device and for capturing data relating to expelling of drug from the injection device. The injection device comprises:
a housing,
expelling means for expelling an amount of drug from the reservoir, comprising:
(i) setting means allowing a user to set a dose amount of drug to be expelled,
(ii) actuation means for releasing the drug expelling means to expel the set dose amount, and
(iii) a mechanical energy storage unit coupled to the actuation means which upon release exerts a driving force for driving the expelling means to expel the set dose amount when the actuation means is actuated,
wherein the expelling means defines a dosing member that moves relative to another component of the injection device during expelling of the set dose amount, the extent of relative movement being indicative of the amount of drug being expelled.

The dose capturing unit comprises a dose sensor adapted to sense said relative movement performed by the dosing member to capture data representing the extent of relative movement of dosing member during expelling of the set dose amount, wherein the dose capturing unit, when attached relative to the injection device, couples to the expelling means of the injection device to exert a counteracting force to the force exerted by the mechanical storage unit to limit the speed of the dosing member at least during a part of the relative movement of the dosing member during expelling of the set dose amount.

For injection devices including a mechanical energy storage unit, such as auto-injectors involving a pre-stressed spring, due to the large amount of energy required for expelling a large dose of a drug, optionally the amount of energy required for expelling the full useable content of a drug cartridge, the force or torque exerted by the mechanical energy storage unit on the movable component is high.

For prior art auto-injectors wherein a component moves rotationally during dose expelling, at certain conditions, components that are rotated in the course of the expelling action may accelerate to reach a rotational speed in the order of 20.000 rpm. Such situation may occur if the auto-injector has not been initially primed, i.e. that the component that drive forward the piston of a cartridge has not been arranged to abut the piston prior to actuation. A similar situation may occur if there is air in the cartridge that prior to actuation has not been removed, i.e. where an initial air shot operation has not been performed. For durable auto-injectors, the high speeds of movements may further occur if the device is actuated when no cartridge is present in the device. Angle speeds of a rotatable component up to 20.000 rpm are particularly difficult to monitor in a reliable and accurate manner. Even though sensors may be designed to read angle speed up to 50.000 rpm such sensors unfortunately require a lot of power.

The injection system of the present invention includes the dose capturing unit that is coupled to a movable component of the injection device and adapted to sense the extent of movement by means of a dose sensor. When coupled to the injection device, the dose capturing unit acts to provide a force on the expelling means that acts counter to the force exerted by the mechanical energy storage unit. Compared to the situation where no dose capturing unit is coupled to the auto-injector, the combined injection device and dose capturing unit limits the speed of rotation occurring during expelling, at least for obtaining a reduction in the peak angle speeds obtained during the expelling operation. This enables use of more simple dose sensing circuitry which enables more cost-effective medical injection systems to be provided. When the dose sensor electronics include an operating scheme that defines a sampling frequency the dose sensors of the dose capturing unit may be configured to use a lower sampling frequency compared to a system that does not include a speed limiting mechanism. The lower sampling frequency means that the dose capturing unit may be operated in a more energy-efficient way than when no speed limiting provisions are at hand.

In some embodiments the dose capturing unit defines a body or casing that accommodates the dose sensor. The body or casing of the dose capturing unit may be releasably attachable relative to the injection device. Due to the fact that components relating to the speed limiting mechanism to a large degree reside in the dose capturing unit, this enables inexpensive manufacture of the injection device. This is particularly the case for disposable injection devices where a drug reservoir is mounted irreplaceably in the injection device. As the dose capturing unit may be provided as a durable part that may be reused in combination with a large number of disposable injection devices, this also reduces the amount of parts that are disposed of potentially leading to less environmental impact.

In further embodiments, the injection device is configured so as to be operable for dose administration (i.e. for dose setting and dose expelling) even when no dose capturing unit is attached relative to the injection device. Hence, the inclusion of a dose capturing system is optional and provides for the possibility of providing first and second versions of the same injection pen where the first version differ from the second version by the parts defining the dose capturing unit. The version of the injection pen that includes the dose capturing unit incorporates the dose capturing unit mounted non-detachably relative to the injection device to form an integrated part of the injection device.

In some embodiments the dose capturing unit comprises a movable mass that couples to the expelling means so that the movable mass is moved when the expelling means is operated. Due to the acceleration of the mass, this provision cause said counteracting force to be exerted on the expelling means effectively reducing the peak speed obtained during an expelling process. As an alternative, or in combination, the dose capturing unit is adapted to be coupled to the expelling means to provide a frictional force for providing said counteracting force.

The speed limiting mechanism for providing said counteracting force may incorporate one or more of the speed limiting mechanisms selected from the group consisting of, a fluidic speed limiter, a fluidic speed limiter utilizing a non-Newtonian fluid, a magnetic brake, an eddy current speed limiter, a centrifugal speed limiter and a clockwork movement optionally incorporating an escapement mechanism. Further speed regulating mechanisms may be incorporated using speed limiting principles disclosed in US 2011/077595, US 2011/0301534 and U.S. Pat. No. 4,921,487.

The dose capturing unit may comprise one or more components that mechanically engage with a component of the expelling means, such as the dosing member, when the dose capturing unit is attached to the injection device.

In some embodiments, the dose capturing unit may include additional means or features that facilitate further functionality of the medical injection system when the dose capturing unit is attached to the injection device. For example, as shown in WO 2013/068483, the dose capturing unit may include a dose limiter for defining a maximum dosage that may be selected by operating a dose setting member of the injection device. Also, in some embodiments, the dose capturing unit may include components that enable operation of the injection device when that particular dose capturing unit is attached to the injection device. The dose capturing unit may be selected from a set of different dose capturing units where each respective dose capturing unit provides a particular specific operating parameter that differs from the remaining dose capturing units of the set. For example, each dose capturing units may include a scale drum having a series of dosage indications where the dosage indications differ throughout the set of dose capturing units. Also, the means for defining maximum and/or minimum limit stops may be defined by the scale drum and hence by the specific choice of dose capturing unit. In still other embodiments, the dose capturing unit may define the size of a dose to be expelled in a fixed way so that the dose capturing unit, when attached to the injection device, facilitates a fixed dose setting that may be prepared during a dose setting or arming procedure prior to the dose expelling procedure. Alternatively, the dose capturing unit include means that couples to the expelling means of the injection device and in this way limits the amount of movement of the expelling means during dose expelling so as to provide expelling of a single or a multitude of a fixed dose administrations only.

The dose capturing unit may in some embodiments comprise electronic detection means for capturing data representing a property related to the amount of drug expelled from the reservoir by the expelling means, either during a single dose administration or during a multitude of dose administrations. The dose capturing unit may include switch means for initiating data capture, where the switch means may be actuated when the injection button of the injection device is activated. In some embodiments, the injection device of the medical injection system includes a coding representing a parameter of the drug to be administered from the reservoir, where the coding is either comprised by the reservoir or by the injection device. The dose capturing unit may include means to detect the coding associated with the particular injection device or reservoir that the dose capturing unit is being attached to. The dose capturing unit may include a memory adapted to store a plurality of recent time-dose logs and optionally associated data related to the parameter of the drug as provided by the coding. The dose capturing unit may also comprise a display adapted to show the time and dose size for the last expelling action, as well as a key allowing a user to e.g. toggle between a plurality of recent time-dose logs. The dose capturing unit may further be provided with an output port for wired or wireless upload of stored data to an external device, e.g. to the users smartphone or a doctors personal computer.

The dose capturing unit may include a coding, such a mechanical and/or electronic coding feature, where the coding determines which of a plurality of different injection devices that the dose capturing unit is compatible with and which of the plurality of injection devices that the dose capturing unit is incompatible with. Hence, the injection device may include means for cooperating with the coding of the dose capturing unit, to either accept or reject attachment or, alternatively, to either accept or reject operability of the medical injection system when a particular dose capturing unit is attached to a particular injection device.

In some embodiments, the dosing member defines a part of the expelling means that is configured to rotate during expelling of a set dose amount. Optionally, the dosing member rotates also during dose setting. For example, the dosing member may rotate in one direction during dialing up a dose, whereas the dosing member rotates in the opposite direction during dialing down a dose and during expelling of a set dose. In addition, the dosing member may be designed to move axially, for example during transition from a dose setting mode to a dose expelling mode and vice versa.

The reservoir adapted for being used by the medical injection system may form a cylindrical cartridge having a piston movable in a distal direction towards an expelling end of the cartridge. Such cartridge has a central longitudinal axis that defines a first axis of the injection device. The dosing member may be configured for rotation around a second axis that is spaced relative to the first axis. The dose capturing unit may in such device be configured to be attached to the injection device at a distal end of the housing of the device. The housing of the device may be formed to define a "doser" apparatus.

The injection device may incorporate a piston rod that is adapted to drive forward the piston of a cartridge. In injection devices of the above mentioned type defining a first and a second axis that are arranged separate from one another, the piston rod may form a flexible piston rod having a first end extending along the longitudinal axis of the cartridge and having a second end that is deflected away from the longitudinal axis of the cartridge.

When the dose capturing unit is mounted to the injection device, the combined apparatus may include a distal facing surface that is defined by a component of the dose capturing unit, such as the body of the dose capturing unit.

The mechanical energy storage unit may be defined by a spring device that is strained to accumulate energy and wherein the accumulated energy upon actuation of the actuation means is released to drive the expelling means to expel the set dose amount from the reservoir.

The dose setting means typically comprises a movable dosage selector that may be operated in a first direction for dialling up a dose and optionally be operated in a second direction for dialling down and reduce an initially set dose. The expelling means may be so configured that the spring device is strained when the dosage selector is operated to dial up a dose.

In other embodiments the mechanical energy storage unit comprises energy sufficient to drive the expelling means for expelling the entire useable contents of the reservoir. Such spring may be tensed already during manufacture so that the user is not required to provide energy to the spring device prior to actuation of the injection device.

In particular embodiments where the dose capturing unit is detachably arranged relative to the injection device, the dose capturing unit is inserted into a cavity of the housing of the injection device, so that a substantial part of the dose capturing unit is accommodated in the housing of the injection device. Examples configurations include configurations wherein more than 25%, such as more than 50%, such as more than 60%, such as more than 80%, such as more than 90% of the volume of the dose capturing unit is accommodated in the cavity of the injection device. In particular embodiments, the entire dose capturing unit is accommodated in the cavity of the injection device so that no part of the dose capturing unit extends beyond the housing of the injection device.

In particular embodiments, the combined apparatus, i.e. the medical injection system in the state where the dose capturing unit is firmly attached to the injection device, the combined apparatus may have a maximum width in a direction transverse to the expelling axis that is less than three times, such as less than two times, such as less than 1.5 times the maximum width of the injection device having no dose capturing unit attached. Also, the combined apparatus may take up volume less than three times, such as less than two times, such as less than 1.5 times the volume the injection device takes up having no dose capturing unit attached.

Also, the combined apparatus may be designed for a peak expelling speed that is less than 90%, such as less than 75%, such as less than 50%, such as less than 25%, such as less than 10% of the peak expelling speed of the injection device having no dose capturing unit attached. Said peak expelling speed of the injection device may be defined as the peak expelling speed obtained during the expelling operation of a dose corresponding to the maximally settable dose amount that the setting means of the injection device allows.

In certain embodiments of the medical injection system, when the dose capturing unit is attached to the injection device, the dose capturing unit provides a casing defining a substantially closed volume wherein a finger of a user cannot touch any of the movable components comprised within the interior of the dose capturing unit.

In the context of the present application, the term "force" encompasses both forces being applied on a component as a linear force as well as a torque being applied on a component tending to cause rotation.

As used herein, the term "drug" is meant to encompass any drug-containing flowable medicine capable of being passed through a delivery means such as a hollow needle in a controlled manner, such as a liquid, solution, gel or fine suspension. Further, "drug" is meant also to encompass mediums for nasal or pulmonary administration. Representative drugs include pharmaceuticals such as peptides, proteins, and hormones, biologically derived or active agents, hormonal and gene based agents, nutritional formulas and other substances in both solid (dispensed) or liquid form. In the description of the exemplary embodiments reference will be made to the use of insulin. Correspondingly, the terms "subcutaneous" and "transcutaneous" injection or infusion is meant to encompass any method of transcutaneous delivery to a subject.

BRIEF DESCRIPTION OF THE DRAWINGS

In the following the invention will be further described with references to the drawings, wherein FIG. 1a is a schematic representation of a first embodiment of a medical injection system in accordance with the invention, FIG. 1b schematically illustrates the working principle of a medical injection system according to the invention, FIG. 2b is a magnified view of section A of FIG. 2a showing the main components of a dose capturing unit 20, FIG. 5a, shows a cross sectional side view of components relating to the drive mechanism of the device shown in FIG. 2a, FIG. 5b is a perspective proximal view of the components shown in FIG. 5a, FIG. 6 is a perspective proximal view of a dose setting member 250 of the device shown in FIG. 2a, FIGS. 7a, 7b and 7c depict detailed perspective views of components 700, 720 and 950 relating to a secondary stop limiter, FIG. 8 shows a perspective cross sectional view of the components of FIGS. 7a, 7b and 7c in an assembled state, FIG. 9 shows a perspective cross sectional partial view of components shown in FIG. 5b, FIG. 10 is a perspective distal view of selected components of FIG. 5b, FIG. 11 is a perspective proximal view of selected components relating to the dose setting and driving mechanism of the injection device 100 of FIG. 2a, and FIG. 12 is a schematic representation of the drive spring of the injection device 100 of FIG. 2a.

DESCRIPTION OF EXEMPLARY EMBODIMENTS

The shown figures are schematic representations for which reason the configuration of the different structures as well as the relative dimensions are intended to serve illustrative purposes only.

In that context it may be convenient to define that the term "distal end" in the appended figures is meant to refer to the end of the injection device which usually carries the injection needle whereas the term "proximal end" is meant to refer to the opposite end pointing away from the injection needle and carrying the dose dial button as depicted in FIG. 1a.

FIG. 1a shows a schematic depiction of an embodiment of a medical injection system for use by a patient for medical self-treatment. The system comprises an injection device 100 being configured for repetitively setting and injecting individually set doses of a drug. FIG. 1a shows a schematic representation of a first embodiment of a medical injection system 100, 20. The injection device 100 includes a housing 110 which along a main axis defines an elongated structure and which at least along a part of its length, in a direction transverse to the main axis, is formed with a non-cylindrical cross section exhibiting a somewhat flat shape, such a device being generally referred to as a "closer" device. In FIG. 1a is further shown a dose capturing unit 20 that in the depicted view is detached from the injection device 100 but which is adapted to be replaceably fitted relative to the injection device 100 by means of a coupling mechanism.

Figure 2A:
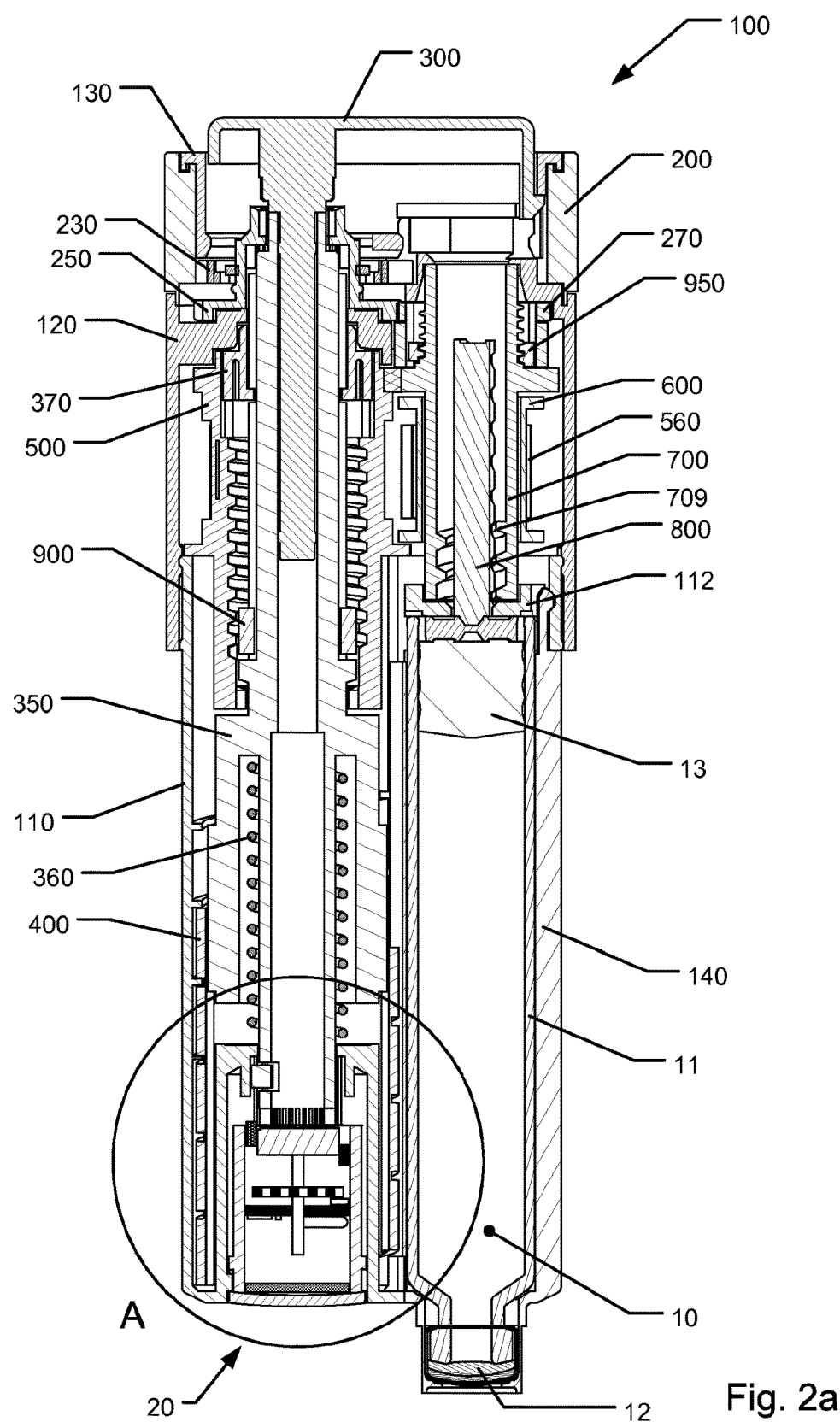
FIG. 2a shows a cross sectional side view of a second embodiment of a medical injection system in accordance with the invention.

The injection device 100 is shown as a cartridge-based injection device wherein a drug filled cartridge 10 is accommodated within the housing 110. Referring to FIG. 2a, the cartridge 10 may be of the type including an elongated cylindrical body 11 and a pierceable septum 12 covering a distal outlet end of body 11 for cooperation with a replaceable subcutaneous injection needle 15. Also, cartridge 10 includes a piston 13 mounted within body 11 for sliding movement along an expelling axis of the cartridge, the expelling axis also defining the rotational longitudinal axis of the cartridge body 11. Either the cartridge 10 or the housing 110 defines a needle mount adapted for releasably mounting a needle assembly 15, e.g. a double pointed injection needle. When a needle assembly 15 is mounted on the cartridge 10 so that septum 12 is pierced, piston 13 may be forced in the distal direction along the expelling axis for expelling portions of the drug accommodated in cartridge 10.

The injection device 100 shown in FIG. 1 further includes a cap 160 which detachably mounts relative to the distal end of housing 110 for protection of the contents of the cartridge 10 and optionally for protecting an injection needle which may be mounted at the distal end of the device.

The injection device 100 incorporates expelling means in the form of a drive mechanism incorporating means for setting a dose and means for expelling a set dose upon actuation of an actuator. The means for expelling a set dose incorporates a mechanical energy storage unit. The actuator includes an injection button 300 arranged at the proximal end of housing 110 adapted to release energy from the mechanical energy storage unit to expel an amount of drug corresponding to the set dose. The means for setting a dose includes a dosage selector in the form of a flexible band 200 that encircles a section of the housing 110 at the proximal end thereof. In the shown embodiment, during a dose setting process, the flexible band 200 may be manually gripped and turned in one direction relative to housing 110 away from an initial position (the zero position) in order to dial up the set dose amount. In order to dial down an initially set dose the flexible band 200 may be turned in the opposite direction back towards the initial position.

Housing 110 further includes a window or opening 170 which provides visual inspection to a mechanically based dose dial scale arranged internally in housing 110. Dose dial scale may be provided as a drum shaped component that includes various printed indicia, such as numerals, arranged thereon, each indicia corresponding to the respective dose sizes that the dose setting part of drive mechanism is designed to assume. The dose dial scale is operated by means of flexible band 200 as it is turned relative to the housing 110 during the dose setting process.

In embodiments where the injection device is adapted for injecting insulin-type medicaments, the dose size may be set as a multitude of fractional or integral numbers of International Units. Typically, the operable control member will have a max dose limit block up to a max dose limit (such as up to 60, 80 or 100 units) wherein a further increase in dose size is being prevented by a blocking mechanism incorporated in the drive mechanism of the injection device 100. If the mechanism is designed to stop expelling when the user stops pushing the injection button 300, the number display in the window will show the portion of the dose (e.g. the numbers of units) not yet expelled, e.g. 10 units of insulin.

The means for expelling a set dose includes a dosing member, i.e. a component (not shown) that during an expelling operation moves relative to another component of the injection device 100. The extent of relative movement of the dosing member is indicative of the amount of drug of the dose expelled.

In the shown embodiment the dose capturing unit 20 is formed to be received in an opening formed in the distal end face of housing 110 so that when the dose capturing unit 20 is coupled with the injection device 100, a substantial part of the dose capturing unit 20 is accommodated within the housing 110 of injection device 100. In the shown embodiment, the dose capturing unit 20 is inserted relative to the injection device along a coupling axis which is parallel to the longitudinal axis of the cartridge. Hence in such configuration the dose capturing unit 20 is placed alongside a needle mount (not shown) of the injection device 100.

The injection device 100 may include a latch mechanism (not shown) which is adapted for locking the dose capturing unit 20 in place once it has been fully inserted into the injection device. The latch mechanism may be configured so that the dose capturing unit snaps in place upon insertion into housing 110 and configured so that when a release button 180 formed at the distal end of housing 110 of injection device 100 is operated, the dose capturing unit 20 is coupled free from the injection device 100. Hereafter, the dose capturing unit may be fitted onto a different injection device. Hence, the dose capturing unit 20 may be configured to be used either with a series of consecutive disposable devices, i.e. prefilled devices, or, alternatively, be used with a durable injection device, i.e. a device wherein the cartridge of the injection device is to be replaced by a new one after the contents of the cartridge has been expelled.

In other embodiments of the dose capturing unit 20 and the injection device 100, the coupling mechanism may include mutually cooperating coupling means different than the latch mechanism indicated above, for example where the dose capturing unit 20 incorporates a latch mechanism internally in a body section of dose capturing unit 20.

The dose data capturing unit 20 comprises electronic detection means for capturing data representing a property related to the amount of drug expelled from the cartridge by the expelling means, and optionally a switch means for initiating data capture, the switch means being actuated when the injection button 300 is moved from its initial to its pushed down position. The dose capturing unit 20 may also comprise a display (not shown) adapted to show e.g. time and dose size for the last expelling action, as well as a key allowing a user to e.g. toggle between a number of recent time-dose logs. The dose capturing unit 20 may further be provided with an output port for wired or wireless upload of data to an external device, e.g. to the users smartphone or a doctors personal computer.

FIG. 1*b* schematically illustrates the working principle of a medical injection system according to the invention. As referred to above the system comprises the injection device 100 which accommodates expelling means 101 inside housing 110. The expelling means includes a dosing member 350 that moves during expelling where the extent of movement is indicative of the amount of drug of the expelled dose. Upon actuation, the expelling means 101 moves one or more components, including dosing member 350 by means of energy being released from a mechanical energy storage unit such as an energized spring, a compressed gas source or the like, i.e. providing an injection device of the auto-injector type.

In FIG. 1*b*, the dosing member 350 rotates during expelling of a dose. Optionally, the dosing member 350 rotates also during dose setting. For example, the dosing member 350 may rotate in one direction during dialing up a dose, whereas the dosing member 350 rotates in the opposite direction during dialing down a dose and during expelling of a dose. In addition, the dosing member 350 may be designed to move axially, for example during transition from a dose setting mode to a dose expelling mode and vice versa.

The injection system of the present invention includes the dose capturing unit 20 that is coupled to the dosing member 350 of the injection device and adapted to sense the extent of movement by means of a dose sensor 20*d*. When coupled to the injection device 100, the dose capturing unit 20 acts to provide a force on the expelling means that acts counter to the force exerted by the mechanical energy unit. In the depicted embodiment, the counteracting force is adapted to act on the dosing member 350 but in other embodiments the counteracting force may be adapted to act on component of the expelling means other than dosing member 350. Compared to the situation where no dose capturing unit is coupled to the auto-injector, the combined injection device 100 and dose capturing unit 20 (i.e. "the combined apparatus") limits the speed of rotation occurring during expelling, at least for obtaining a limitation in the peak value of the speed obtained during the expelling movement.

The counteracting force emanating from the combined injection device 100 and dose capturing unit 20 may be provided by various different principles either acting alone or in combination. In FIG. 1*b*, "M" designates a mass that is coupled to dosing member 350 and which due to being accelerated by dosing member 350 during expelling of a set dose acts to create a drag force on dosing member 350. In FIG. 1*b* "F" designates a frictional force that is being applied on an element that rotates when the dosing member 350 rotates. Such friction may be obtained by a brake mechanism involving friction directly on dosing member 350 or alternatively involving friction acting on a component that is mounted within dose capturing unit 20 and being a part of dose capturing unit where this component rotates in synchronism with the dosing member 350 during the expelling action.

Exemplary speed limiting principles may be involved alone or in combination by configuring the combined apparatus to incorporate brake mechanisms such as an inertia brake, a friction brake, a fluidic brake, a magnetic brake, an eddy current brake and a centrifugal speed limiter. Other speed limiting mechanisms such as a clockwork movement may be provided. Such speed regulating means may include an escapement mechanism.

Figure 3A:
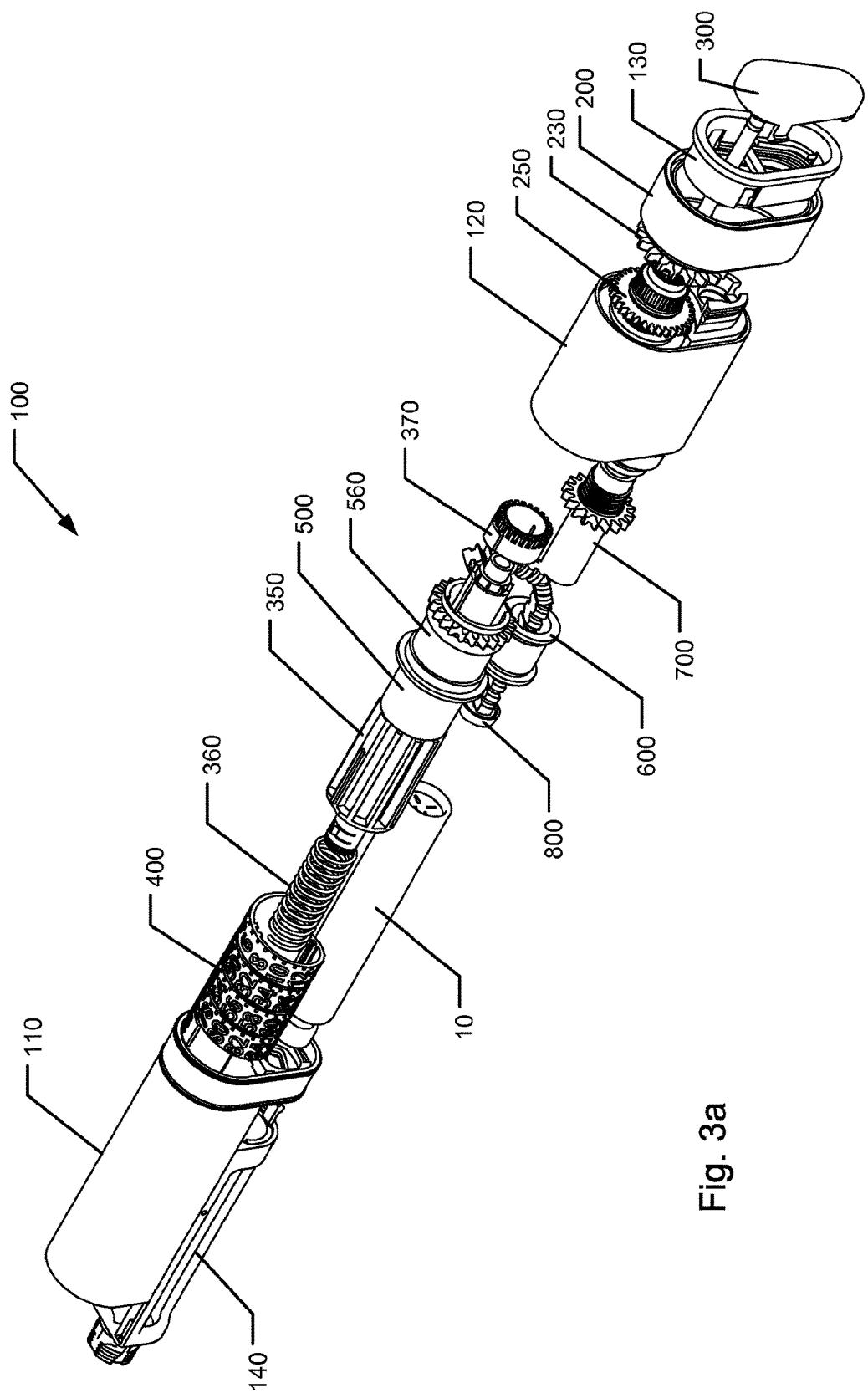
FIG. 3a shows an exploded perspective view of the main components of the injection device 100 of FIG. 2a, FIG. 3b shows an exploded side view of the main components of the injection device 100 of FIG. 2a, FIG. 4a is a cross sectional side view of the device of FIG. 2a in an initial state before the setting of a dose.
Figure 3B:
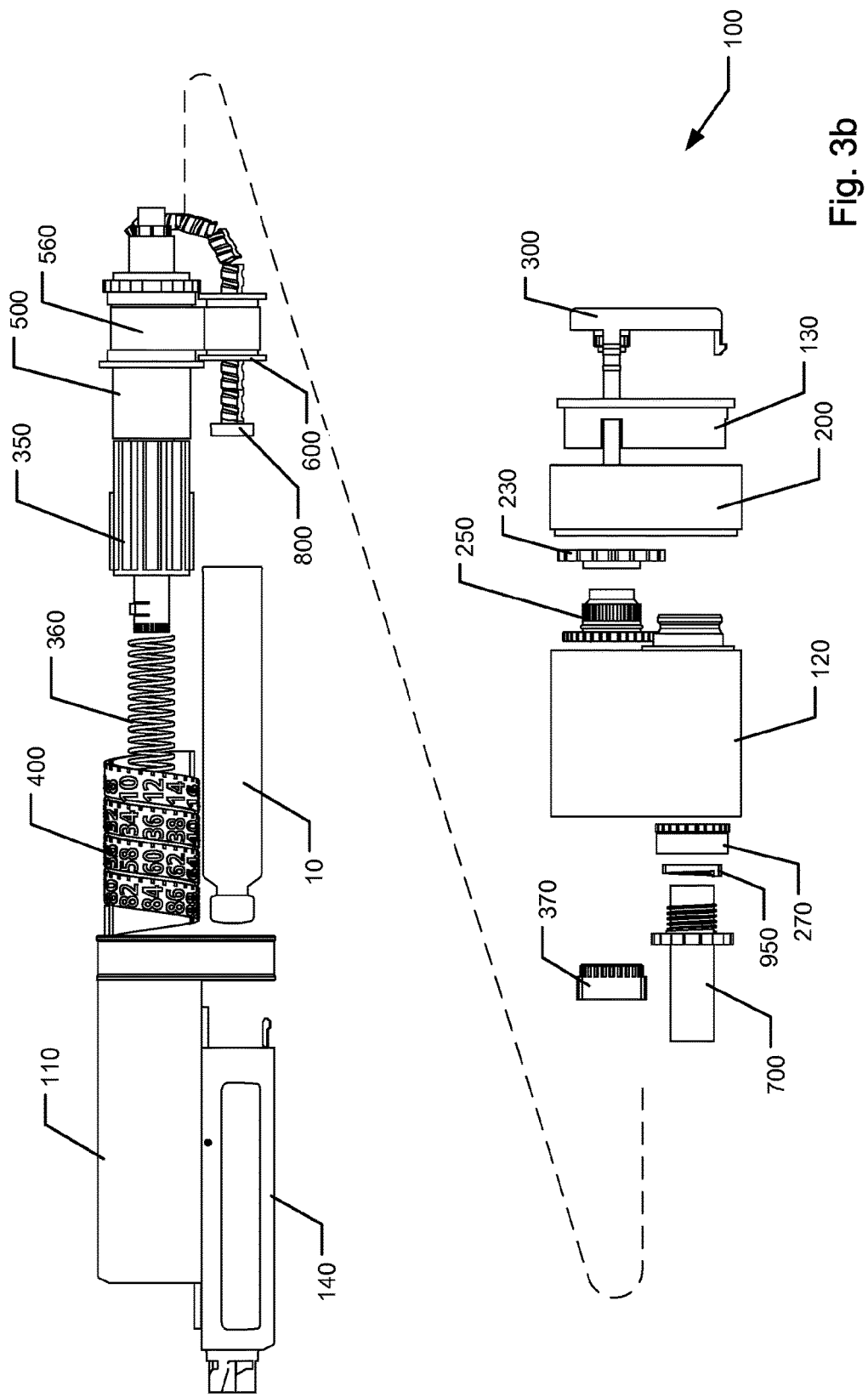

Reference is now made to FIG. 2a which shows a cross sectional detailed side view of an example embodiment of a medical injection device 100 cooperating with an example dose capturing unit 20 according to the invention. FIG. 2a only includes references referring to the main components. Exploded perspective and cross-sectional views of the main components of the injection device 100 shown in FIG. 2a are depicted on FIGS. 3a and 3b. For further details to each of the components of injection device 100 reference is made to the remaining figures, in particular FIGS. 4a-4d. The dose capturing unit 20 will be described further below in the closing part of the description section of the application.

The housing (110,120,130,140) comprises a distal housing part 110, an intermediary housing part 120, a proximal housing part 130 and a cartridge housing part 140. Further, as depicted in FIGS. 4a-4d, a distal opening arranged adjacent the needle mount may include a cover section 150 covering an internal cavity of the distal part of the housing. The cover section 150 is removably attached to distal housing part 110. As described later the cover section 150 can be replaced by a dose capturing unit 20 that is insertable into the internal cavity. Injection device 100 further comprises expelling means comprising a dose injection mechanism operable by an injection button 300 and a dose setting mechanism operable by a dosage selector 200.

The dose injection mechanism comprises a piston rod 800 that engages the piston 13 (by means of a piston washer). Piston rod 800 extends axially in the proximal direction away from piston 13. In the shown embodiment, the piston rod 800 is of a flexible type having a piston engaging end and a free end wherein the flexibility is provided by forming the piston rod of a series of interconnected links. The flexibility allows the free end of the piston rod to be deflected away from the expelling axis. It is to be noted that FIG. 2a and FIGS. 4a-4d only show the most distal part of piston rod 800, the remaining parts of piston rod 800 is for clarity reasons omitted from these drawings. However, the structure of piston rod 800 is more clearly depicted in FIGS. 3a and 3b where it can be seen that, in the depicted operating state for the piston rod 800, the piston engaging end of the piston rod 800 assumes a straight portion while the free end assumes a bended portion.

In the shown embodiment, the piston rod 800 is a segmented type rod that consists of interconnected hinged rod elements that are adapted to swivel relative to each other at least in a particular direction of rotation so that the free end of the piston rod 800 may bend away from the expelling axis. When parts of the piston rod 800 assume a straight configuration, the rod elements are substantially incompressible so that the piston rod 800 is able to act as a push rod. Along its longitudinal extension piston rod 800 defines a first track and a second track each adapted to cooperate with a respective one of a nut member and a rotation control member so that relative rotation between the nut member and the rotational control member results in a longitudinal movement of piston rod 800. In alternative embodiments, the piston rod may be formed as a coiled axially incompressible spring which along its length is deflected away from its neutral rectilinear shape and that serves to transfer forces to the piston of the cartridge.

In the shown embodiment, the first track of the piston rod 800 defines an external thread (not referenced) and the second track (not referenced) defines a rotation control geometry that cooperates with a guide member 112 formed in distal housing part 110 to ensure that at least the straight portion of piston rod 800 is kept substantially in-rotatable. The rotation control geometry of the piston rod 800 may for example include one or more planar portions adapted to mate with a cooperating structure of the guide member 112 so as to prevent rotation between the piston rod 800 and the cooperating guide member 112.

As shown in FIG. 2a, the dose injection mechanism of injection device 100 comprises a drive nut 700 having an internal thread 709 that engages the external thread of the piston rod 800. Drive nut 700 is mounted rotatably free but axially fixed relative to the housing so that drive nut 700 is able to rotate around the expelling axis, the amount of rotation of drive nut 700 thereby being decisive for the axial distal displacement of the straight portion of the piston engaging end of the piston rod 800.

The dose injection mechanism further includes a drive member 500 that is mounted rotatable but axially fixed relative to the housing, the drive member 500 being in rotational engagement with drive nut 700 so that the drive nut 700 rotates as the drive member 500 rotates. An actuator providing a stored energy source exerts a substantially constant driving force on drive member 500 in the particular direction of rotation that enables the piston rod 800 to be driven in the distal direction. In the shown embodiment, the stored energy source comprises a drive spring 560 in the form of a flat spiral spring that initially is stored on a storage drum 600 and which spools onto the drive member 500 as the energy accumulated in the drive spring 560 is released for driving the piston rod 800 in the distal direction. As regards further details of the drive mechanism reference is made to the discussion further below in relation to FIGS. 10 and 11.

As noted above, injection device 100 further includes a dose setting mechanism allowing a user to set a desired dose to be injected by means of the dose injection mechanism.

Coupled to the dose setting mechanism and the dose injection mechanism is a clutch mechanism that ensures that during dose setting, no movement of the drive mechanism is possible and that ensures that during dose injection the dose setting cannot be manipulated to alter a dose setting that has previously been set. Hence the clutch mechanism defines the injection device 100 to be operated in a dose setting mode and in a dose expelling mode. In the shown embodiment the clutch mechanism includes four separate clutch engagement mechanisms. In FIGS. 4a-4d and in the following discussion these four clutch engagement mechanisms are respectively designated a first, second, third and fourth clutch engagement (C1, C2, C3, C4).

The injection button 300 is arranged to protrude in a proximal direction from the proximal housing part 130 and arranged for limited axial movement between a default proximal position and a distal pressed down position. The mode of the clutch mechanism is controlled by the injection button 300. When the injection button 300 is depressed into the distal position the injection device 100 is in dose expelling mode whereas when the injection button 300 assumes its default proximal position the injection device is in dose setting mode. The injection button 300 is arranged relative to the housing of the device 100 so that the injection button 300 cannot rotate.

The clutch mechanism includes a drive clutch 370 mounted between the drive member 500 and the housing part 120 that controls whether or not drive member 500 is allowed to rotate relative to the housing. The clutch mechanism will be described in greater detail further below.

The dose setting mechanism comprises a dose setting member 250 that is manually operable by turning operable dosage selector 200. Dose setting member 250 is axially fixed relative to the housing but rotates around an axis defining a dose setting axis that extends in parallel with the expelling axis but is separated from the expelling axis by a certain distance. A dosage selector connector 230 couples movement of dosage selector 200 with rotation of the dose setting member 250 so that the dose setting member 250 may be rotated in either direction controlled by movement of the dosage selector 200. Between dosage selector connector 230 and dose setting member 250, a slip coupling may be arranged to prevent destruction on the mechanism in case excessive forces are being applied on dosage selector 200. In the shown embodiment, as more clearly indicated on FIG. 3a, dosage selector 200 is arranged along a cross section transverse to the expelling axis of the housing i.e. between intermediary housing part 120 and proximal housing part 130. Dosage selector is formed as an endless flexible band 200 that generally conforms to the shape of the exterior surfaces of housing parts 120 and 130 due to the engagement with guiding structures formed in housing parts 120 and 130. Hence, the flexible band 200 may be moved along the directions of circumference of the flexible band in a first direction to increase the setting of a dose and in the opposite direction for decreasing an already set dose. An interior surface of the flexible band 200 forms a series of teeth that cooperate with dosage selector connector 230 to transform movement of flexible band 200 into a rotation of dose setting member 250. In other embodiments, instead of a flexible band 200 the dosage selector may be provided as a wheel or knob that may be manually turned for operating the dose setting mechanism. The dosage selector may for example be formed by dose setting member 250 by arranging openings in the housing of the device suitable formed to allow manual manipulation of dose setting member 250.

Further, the above mentioned dosing member is defined by a dose control member 350 that extends longitudinally along the dose setting axis. The dose control member 350 is arranged in the housing for limited axial movements between a proximal position and a distal position. A pin 310 of injection button 300 extends distally from injection button 300 along the dose setting axis and into an opening of dose control member 350. Pin 310 serves to couple axial movements of the injection button 300 with axial movements of dose control member 350 but allows the dose control member 350 to be rotated around the dose setting axis.

A compression spring 360 is arranged in the housing to exert a proximally directed force on the dose control member 350 to bias the dose control member 350 and hence the injection button 300 into the proximal (default) position.

Positioned coaxially with the dose control member 350 and in distal housing part 110 is a dose dial scale 400 arranged. In the shown embodiment, the dose dial scale 400 is provided as a tubular sleeve that defines an exterior thread 407 engaging an interior thread 117 formed in distal housing part 110 (see FIG. 4a). Along an exterior helical path, the dose dial scale 400 is provided with a series of numerals each referring to individually selectable doses of a drug that the injection device 100 is designed to set and to expel. Housing part 110 is provided with an opening or window (not shown) through which a current dose setting is viewable.

Dose dial scale 400 is adapted to rotate together with the dose control member 350 but dose dial scale 400 is movable in axial directions relative to dose control member 350. In the shown embodiment this function is facilitated by means of an interior surface of the dose dial scale 400 that defines one or more axially extending tracks 401 that cooperate with corresponding one or more axially extending tracks 351 formed on an exterior surface of the dose control member 350 (see FIGS. 4a and 11).

Dose dial scale 400 includes a minimum limiting stop surface and a maximum limiting stop surface that define two extreme end positions that dose dial scale may assume during operation of the injection device 100 preventing operation outside the two extreme end positions. As best viewed in FIG. 3b, dose dial scale 400 includes said two stop surfaces as axially extending ledges (non-referenced) that each is adapted to cooperate with a respective dose stop surface defined by distal housing part 110 and intermediary housing part 120. In the shown embodiment, dose dial scale 400 is adapted to experience a total rotation of 3.5 turns relative to the housing between a zero dose position and a maximum dose position. In the shown embodiment the dose dial scale 400 is provided with 100 separate dose markings along a helical path.

Dose control member 350 serves several functions relating both to the dose setting mechanism and to the dose injection mechanism of injection device 100.

When the injection device 100 is in dose setting mode, i.e. when the injection button 300 is in the default proximal position, dose control member 350 couples a rotation of the dose setting member 250 with rotation of the dose dial scale 400.

When the injection device 100 is in dose expelling mode, i.e. when the injection button 300 is in the pushed down position, the dose control member 350 couples rotation of the drive member 500 with rotation of the dose dial scale 400.

Dose control member 350 further includes a resilient tooth 359 (see FIG. 4a) adapted to engage a series of axial splines 119 formed in the distal housing part 110. The resilient tooth 359 and the splines performs as a click mechanism that makes the dose setting occur in discrete steps, e.g. corresponding to the number of numerals provided on the dose dial scale 400. During dose setting, the injection device 100 hereby emits a series of clicks as the dosage selector 200 is manipulated. In addition, as a dose of drug is being expelled, the click mechanism emits a series of click sounds as the dose control member 350 is rotated, e.g. one click as each unit of doses being expelled. Due to the axial splines 119, the dose control member 350 is allowed to move axially without this having influence on the performance on the click mechanism.

Besides the above functions, also the function of the drive clutch 370 is coupled with movements of the dose control member 350. In addition an end of content mechanism (EOC) including an EOC track follower 900 is coupled to the movement of dose control member 350. As will be appreciated by a person skilled in the art, an end of content mechanism is a mechanism which prevents the setting of a dosage amount which exceeds the useable dose amount remaining in the drug cartridge.

The function of the drive clutch 370 is provided by means of a second clutch engagement C2 (122, 372) between the drive member 500 and the intermediary housing part 120. Drive member 500 and drive clutch 370 are rotationally locked relative to each other so that they rotate together but drive clutch 370 may be moved slightly in the axial direction relative to the drive member 500. Between drive clutch 370 and dose control member 350 is a coupling which ensures that the axial movements of drive clutch 370 follows axial movements of the dose control member 350 but relative rotational movement between these two components is enabled. Drive clutch 370 includes a series of teeth 372 adapted to engage corresponding teeth 122 formed in the intermediary housing part 120 (see FIGS. 4a, 4c and 11). Hence, when the injection button is in the proximal position, the drive member 500 is locked relative to the housing so that rotation of drive member 500 is prevented. Upon depression of injection button 300, the drive member 500 is released from the rotational locking relative to the housing allowing the drive member 500 to rotate. Hence, only when the injection button is depressed the drive member 500 is allowed to rotate and an expelling operation is enabled.

A first clutch engagement C1 (502, 352) is provided between the drive member 500 and the dose control member 350. The drive member 500 defines a distal circular opening along which a series of teeth 502 are arranged (see FIGS. 4a and 10). The dose control member 350 includes a series of corresponding teeth 352. When the dose control member 350 is in its distal position (see FIG. 4c), the teeth 352 of dose control member 350 engage with the teeth 502 of drive member 500 to effectively lock the two components against relative rotation. Hence when the injection button 300 is pushed down during dose injection, the rotation of the drive member 500 is coupled with rotation of dose control member 350. When the dose control member 350 is moved into its proximal position (see FIGS. 4a, 4b and 4d), the teeth 352 are moved out of engagement with the teeth 502 of drive member 500. Hence when the injection button 300 is released, rotation of the dose control member 350 relative to drive member 500 is enabled.

Figure 4A:
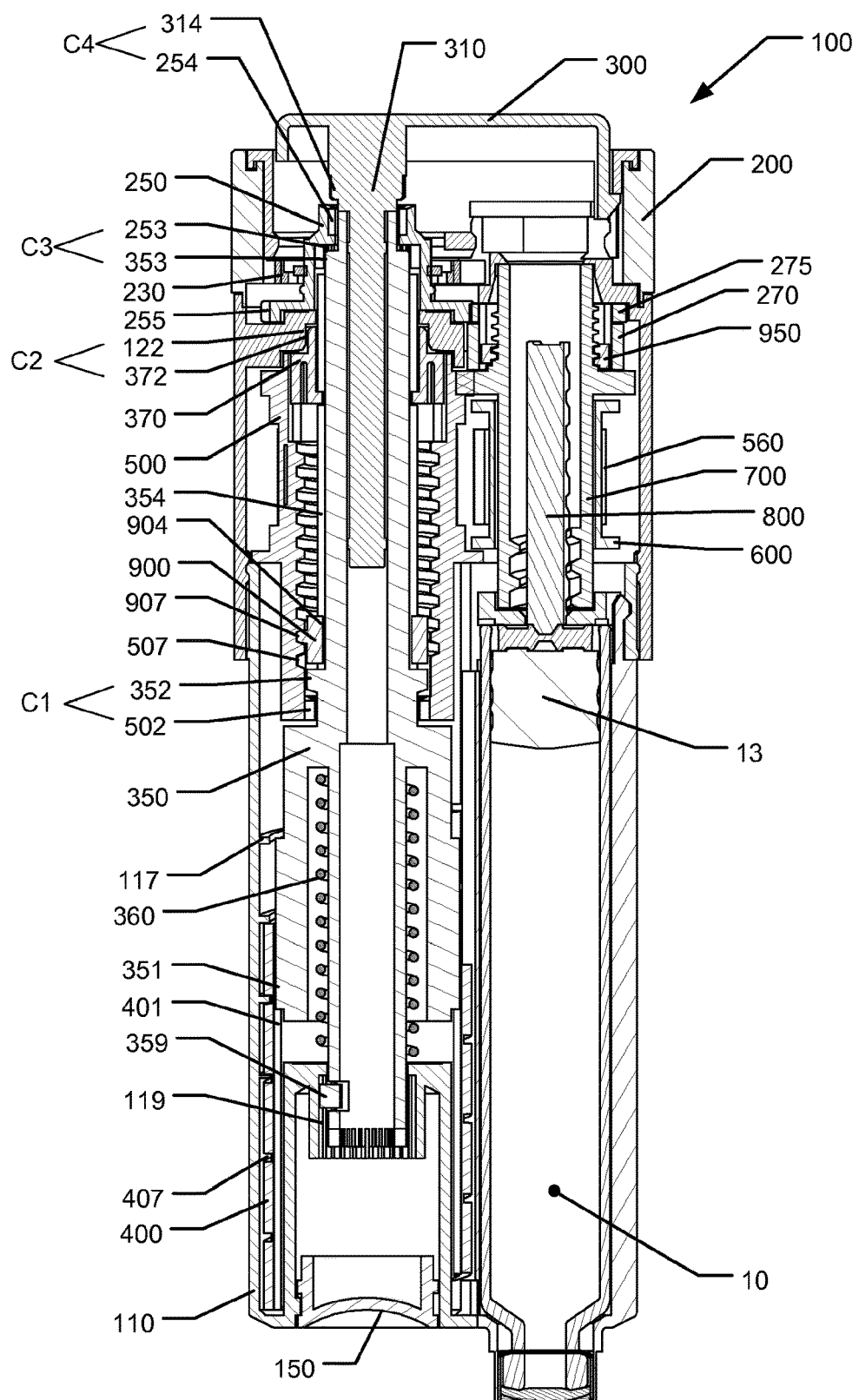
FIG. 4b is a cross sectional side view of the device of FIG. 2a where a dosage selector 200 has been operated to set a particular size of a dose.
FIG. 4c is a cross sectional side view of the device of FIG. 2a where an injection button 300 has been pushed down and where the injection of the set dose has been completed.
FIG. 4d is a cross sectional side view of the device of FIG. 2a after the completion of the injection of the set dose and wherein the injection button has been released.

A third clutch engagement C3 (253, 353) is provided between the dose setting member 250 and the dose control member 350. The proximal part of dose control member 350 includes a series of teeth 353 (see FIG. 4a and FIG. 11) adapted to engage corresponding teeth 253 formed in dose setting member 250 (see FIGS. 4a, 5a and 6). When the dose control member 350 is in its proximal position, the teeth 353 of dose control member 350 engage with the teeth 253 of dose setting member 250. Hence, during dose setting, and when the injection button 300 is in its released position as shown in FIG. 4a, the dose setting member 250 is coupled with the dose control member 350 so that these component rotate together. When the dose control member 350 is moved into its distal position as shown in FIG. 4c, the teeth 353 are moved out of engagement with the teeth 253 of dose setting member 250. Hence when the injection button 300 is pushed down, rotation of the dose control member 350 relative to dose setting member 250 is enabled.

A fourth clutch engagement C4 (254, 314) is provided between the dose setting member 250 and the injection button 300. Dose setting member 250 defines a proximal circular opening along which a series of teeth 254 are arranged (see FIGS. 4a, 5a and 6). The distally extending pin 310 of injection button 300 includes a series of corresponding teeth 314 (see FIGS. 4a-4d). When the dose control member 350 is in its distal position (shown in FIG. 4c), the teeth 314 of injection button 300 engage with the teeth 254 of the dose setting member 250 to prevent relative rotation between dose control member 350 and injection button 300. Button 300 is prevented from rotational movement relative to proximal housing part 130. Hence, when the injection button 300 is pushed down, such as during dose injection, rotation of the dose setting member 250 relative to the housing is prevented. In the disclosed embodiment the dosage selector 200 cannot be operated during dose injection. When the dose control member 350 is moved into its proximal position (shown in FIGS. 4a, 4b and 4d), the teeth 314 are moved out of engagement with the teeth 254 of the dose setting member 250. Hence when the injection button 300 is released, rotation of the dose setting member 250 relative to the housing is enabled which allows for a dose to be set by operating dosage selector 200.

As shown in FIGS. 4a, 5a and 5b the drive member 500 includes a cylindrical section forming a gear wheel 505. Also the drive nut 700 includes a cylindrical section forming a gear wheel 705 that engages gear wheel 505. Hence a rotation of drive member 500 in a particular direction during dose injection is transferred to rotation in the opposite direction of drive nut 700.

Figures 10, 11, 12:
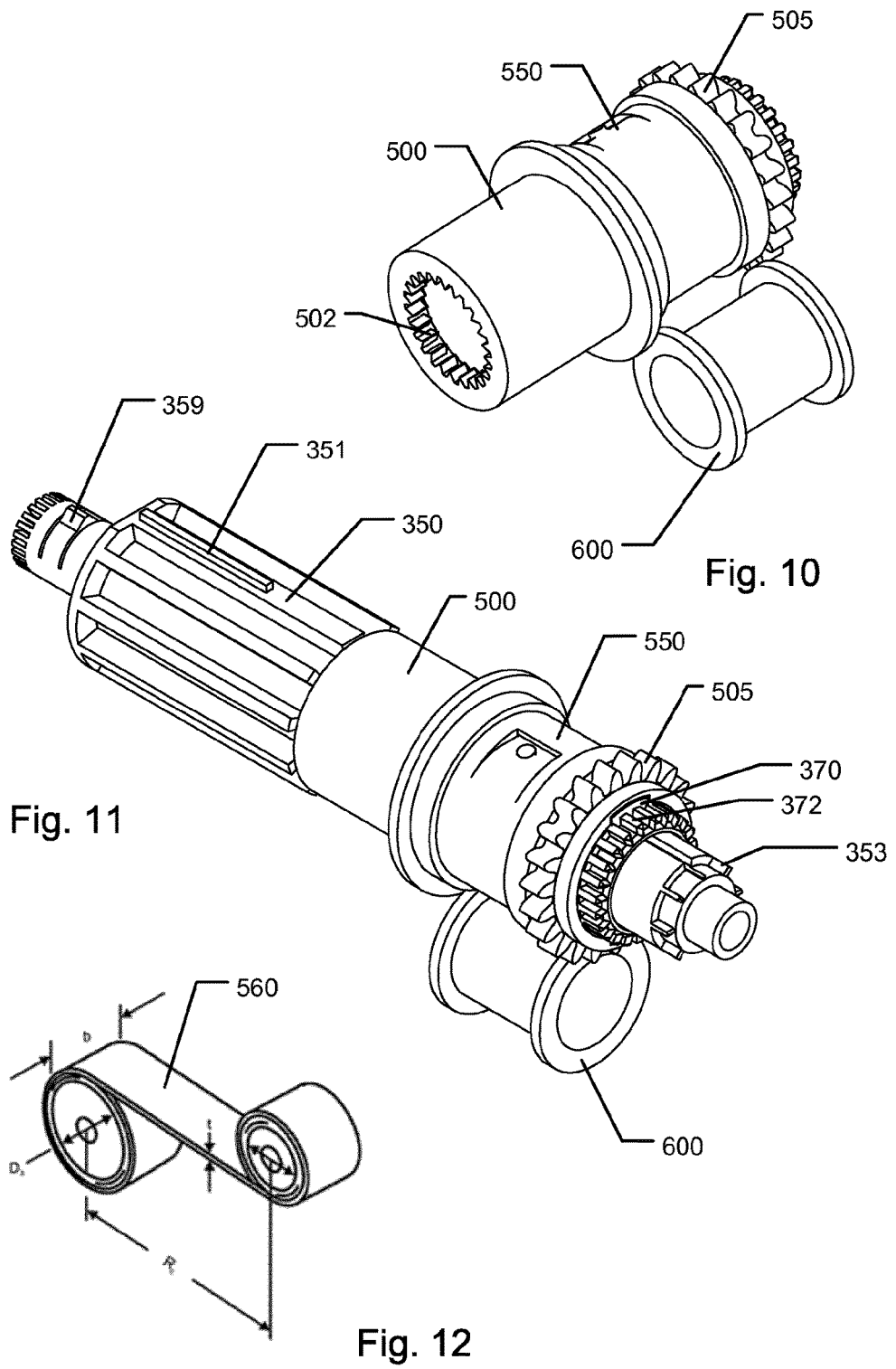

FIGS. 10 and 11 show perspective representations of selected components of the drive mechanism included in injection device 100.

The drive member 500 includes a further cylindrical spring receiving section 550 that is arranged to reside next to the storage drum 600 in the same axial position in the housing of the device as the storage drum 600. Drive nut 700 provides a bearing surface adapted to receive storage drum 600 so that storage drum may rotate independently relative to the drive nut 700. In this embodiment, the drive spring 560 is provided as a constant force spring arranged between the storage drum 600 and the cylindrical spring receiving section 550 of drive member 500. The spring 560 may be arranged to constitute an S-shaped curve in a manner schematically shown on FIG. 12. The drive spring 560 may be adapted to have a natural tendency to reside on the storage drum 600. However, during production of the injection device 100 the drive spring 560 is forced onto the cylindrical spring receiving section 550 thereby accumulating energy in drive spring 560. Upon release, the accumulated energy of the drive spring 560 urges drive member 500 to rotate while the drive spring 560 gradually winds up onto storage drum 600. The cylindrical spring receiving section 550 includes means (non-referenced) to fasten the end of the drive spring 560 so that slippage between the drive spring 560 and drive member 500 will not occur.

In other embodiments, the direction of movement may be reversed so that the drive spring 560 may gradually seek to move onto the drive member 500 during energy release, i.e. during dose expelling. Also other configurations of drive springs than the shown S-type spring may be used.

In the shown embodiment, the drive spring 560 is fully loaded during the assembly of the injection device 100. When purchased by the user, the drive spring contains sufficient energy to deliver the entire useable amount of drug contained in the cartridge 10.

During dose setting, the dose control member 350 is rotated in accordance with the dose set as adjusted by means of dosage selector 200. This has the effect that the dose dial scale 400 is rotated away from its zero dose position. The amount of rotation of dose dial scale 400 therefore exactly corresponds to the selected dose size. During this movement the first clutch engagement C1 is in the released state so that the drive member 500 is not being operated. It is noted that during dose setting, the second clutch engagement C2 is engaged meaning that the drive member 500 is prevented from rotating.

The dose setting may be performed by dialling up and down dosage selector 200 until a desired dose shows up in the dose window of the housing. After the desired dose has been dialled, and after an injection needle has been mounted relative to the drug cartridge 10, the desired dose is ready for injection.

After applying a suitable force on the injection button 300 to press down the injection button to the distal position, the first clutch engagement C1 is in the engaged state and the second clutch engagement C2 is in the released state. Hence, the drive member 500 is released for rotation relative to the housing and is urged by spring drive 560 to rotate thereby carrying with it the dose control member 350. As long as the injection button 300 is maintained in the depressed position, the drive member 500, the dose control member 350 and the dose dial scale 400 rotate together towards the zero dose position. All this time the drive nut 700 rotates to drive forward the piston rod 800 resulting in the expelling of the drug through the attached needle. The movement is stopped when the minimum limiting stop surface of the dose dial scale 400 engages the corresponding dose stop surface formed in distal housing part 110. This simultaneously stops the drive member 500 from rotating and the piston rod 800 will move no further.

It is to be noted that during dose injection procedure, the expelling may be halted at any time by releasing pressure on the injection button 300. The expelling may be continued by renewed pressing down the injection button 300.

Hence the dose dial scale 400 acts as a metering device during dose setting where the return movement of the dose dial scale 400 during injection determines the amount that will be expelled. In this way the dose dial scale provides a primary stop limiter.

The injection device 100 further includes a secondary stop limiter which performs as a safety back up function in case that a mechanical error occurs somewhere in the dose setting mechanism or somewhere in the dose injection mechanism. In the shown embodiment, the drive nut 700 is associated with such a secondary stop limiter. As apparent from FIG. 2*a* and in particular FIGS. 5*a*-5*b*, 7*a*-7*c*, 8 and 9 the secondary stop limiter includes the said drive nut 700, a secondary stop ring 270 arranged coaxially with the drive nut 700 and a secondary stop track follower 950 arranged between the drive nut 700 and secondary stop ring 270.

As shown in FIG. 7*a*, the drive nut 700 includes an external thread 707 provided on a proximal cylindrical portion thereof. The drive nut 700 defines a stop surface 708 located at a particular position relative to the thread 707.

Referring to FIG. 7*b*, the secondary stop track follower 950 is in this embodiment in the form of a cylindrical nut that defines an internal thread 957 adapted to engage the thread 707 of drive nut 700. The secondary track follower 950 defines a stop surface 958 that is adapted to engage the stop surface 708 provided on drive nut 700 for a particular relative rotational and axial position between the secondary stop track follower 950 and drive nut 700. The secondary stop track follower 950 further comprises one or more track elements 953 extending radially outwards from an outer cylindrical surface of secondary stop track follower 950.

As shown in FIG. 7*c*. the secondary stop ring 270 is a generally cylindrical sleeve that includes a cylindrical bearing surface (non-referenced) adapted to be rotatably supported in the housing at a fixed location thereof. An interior surface of the stop ring 270 includes one or more axially extending tracks 273 each of which is adapted to cooperate with respective ones of track elements 953 of the secondary stop track follower 950. In this way the secondary stop track follower 950 is configured to rotate with the secondary stop ring 270 but allows relative axial displacement of secondary stop track follower 950 relative to secondary stop ring 270. A cylindrical section of secondary stop ring 270 forms a gear wheel 275 that is adapted to engage the gear wheel 255 section of dose setting member 250.

In the assembled state the drive nut 700, the secondary stop ring 270 and the secondary stop track follower 950 forms an assembly that more easily is viewed in FIGS. 5*a*, 8 and 9.

Due to the threaded engagement between the secondary stop track follower 950 and the drive nut 700, the secondary stop track follower 950 will be moved back and forth in the axial direction as the secondary stop track follower 950 and the drive nut 700 rotate relative to each other.

Before the setting of a dose, when the dose dial scale 400 indicates its zero dose setting through the window in the housing, the secondary stop track follower 950 will assume an initial position relative to the drive nut 700. In this state the stop surface 958 of the secondary track follower 950 will be situated in close proximity with respect to the stop surface 708 provided on drive nut 700. As a dose is dialled up by manipulating dosage selector 200 the dose setting member 250 will be rotated and, due to the engagement between gear wheel 255 and gear wheel 275, the secondary stop ring 270 and the secondary track follower 950 will be rotated as well. As the drive nut 700 is maintained non-rotatable during dose setting, due to the threaded connection 707 and 957, the secondary track follower 950 will be moved in the proximal direction so that the stop surface 958 of the secondary track follower 950 will be moved further away from the stop surface 708 provided on drive nut 700.

During dose injection, when the injection button 300 is pressed down, the dose setting member 250 is prevented from rotating and hence the secondary stop ring 270 and the secondary track follower 950 are prevented from rotating as well. However, as the drive nut 700 rotates during injection, due to the threaded connection 707 and 957, the secondary track follower 950 will be moved in the distal direction.

In a correctly working injection device 100, upon reaching the end of dose state where the dose dial scale 400 is located so that its minimum limiting surface engages the corresponding dose stop surface defined by the distal housing part 110 (corresponding to the zero dose position), the secondary track follower 950 will be moved to assume the initial position as referred to above. In this position the stop surface 958 of the secondary track follower 950 will again be situated in close proximity with respect to the stop surface 708 provided on drive nut 700.

In case a mechanical failure occurs in the injection device, such as a failing primary stop limiter, a failing first clutch engagement C1 or a failing second clutch engagement C2, the biasing force exerted by the drive spring 560 on drive member 500 may cause the drive member to run freely causing the drive nut 700 to rotate and the piston rod 800 to move in the distal direction in an uncontrolled manner. However should such a situation arise, the drive nut 700 may slightly rotate but soon the secondary stop limiter will prevent further rotation of drive nut 700 as the stop surface 958 of the secondary track follower 950 will be in abutment with the stop surface 708 provided on drive nut 700.

In the shown embodiment, the drive nut 700 defines a thread 707 whereas the stop ring 270 defines one or more axially extending tracks 273 where the thread 707 and the tracks 273 engage corresponding structures on the secondary track follower 950. A similar function may be obtained by rearranging the thread to be disposed on the stop ring 270 and the axially extending tracks to be disposed on the drive nut 700 and rearranging the structures on the secondary track follower 950 accordingly. In still other embodiments, the secondary track follower 950 defines two threaded sections where each of the threaded sections operate with corresponding threads formed on the drive nut 700 and the stop ring 270 respectively. In such embodiment, the two threaded engagements are provided with differently pitched threads so that the secondary track follower 950 is forced to move axially as the drive nut 700 and the stop ring 270 rotate relative to each other.

In the shown embodiment, the secondary track follower 950 is formed as a cylindrical nut. In alternative embodiments, the secondary track follower 950 may alternatively be provided as a half-nut or forming another structure such as ball clamped between tracks formed in the drive nut 700 and the stop ring 270 where the tracks have different pitches.

The above mentioned end of content (EOC) mechanism will now be more fully described referring generally to FIG. 4a. In the shown embodiment, the dose control member 350 includes one or more longitudinal extending ribs 354 provided along an exterior cylindrical surface thereof. The drive member 500 includes an interior cylindrical surface that defines an interior thread 507. And end of content track follower (EOC track follower) 900 is formed as a cylindrical nut and arranged coaxially with the drive member 500 and the dose control member 350 so that the EOC track follower is located between the drive member 500 and the dose control member 350. The EOC track follower 900 defines an external thread 907 that cooperates with internal thread 507 of drive member 500. EOC track follower 900 further defines one or more internal axial recesses each adapted to cooperate with the one or more longitudinal extending ribs 354 of dose control member 350.

A not shown EOC limitation stop is associated with a proximal part of the thread 507 of drive member 500. In a known manner such stop may define a rotational stop surface adapted to engage a rotational stop surface (not shown) of the EOC track follower 900 for a particular relative axial and rotational position between the EOC track follower 900 and the drive member 500. The said EOC limitation stop limits the movement of the EOC track follower 900 in the proximal direction so that the settable size of the dose is limited to dosage amounts to which a corresponding dosage remains in the cartridge 10. In this way the dosage selector 200 cannot dial up a dose that is larger than the remaining useable dose accommodated in the cartridge.

Prior to use of the injection device, where the cartridge 10 is full and the piston rod 800 is located in the position shown on FIG. 4a, the EOC track follower 900 is positioned in an initial axial position relative to the housing (see FIG. 4a). During dialling up a dose the EOC track follower 900 is rotated as the dose control member 350 rotates relative to the drive member 500. Due to the threaded engagement 507, 907, the EOC track follower is moved in the proximal direction as a dose is dialled up (see FIG. 4b). Should the dosage selector 200 be moved for dialling down a previously set dose, the EOC track follower 900 will move in the distal direction in accordance with the reduction in dose size.

When an injection is initiated, the dose control member 350 will move to its distal position. This has no influence on the axial position of the EOC track follower 900. During injection wherein the first clutch engagement C1 is in the engaged state, the dose control member 350 rotates along with the drive member 500. Hence, during this procedure, the EOC track follower 900 will retain its position relative to the thread 507 defined by the drive member 500 (see FIG. 4c).

Finally, after the dose injection has been completed, the injection button 300 is released and the first clutch engagement C1 is disengaged and the second clutch engagement C2 is engaged. Again, this has no influence on the axial position of the EOC track follower 900 (see FIG. 4d).

After additional subsequent dose setting and dose injection procedures the EOC track follower will move gradually in the proximal direction in accordance with the accumulated dialling up procedures during each of the performed administrations. As noted above, at a predetermined point the EOC track follower will abut an EOC limitation stop which will prevent further dialing up. Hereby the user is notified that the cartridge does not contain sufficient doses above a certain limit.

Figure 4B:
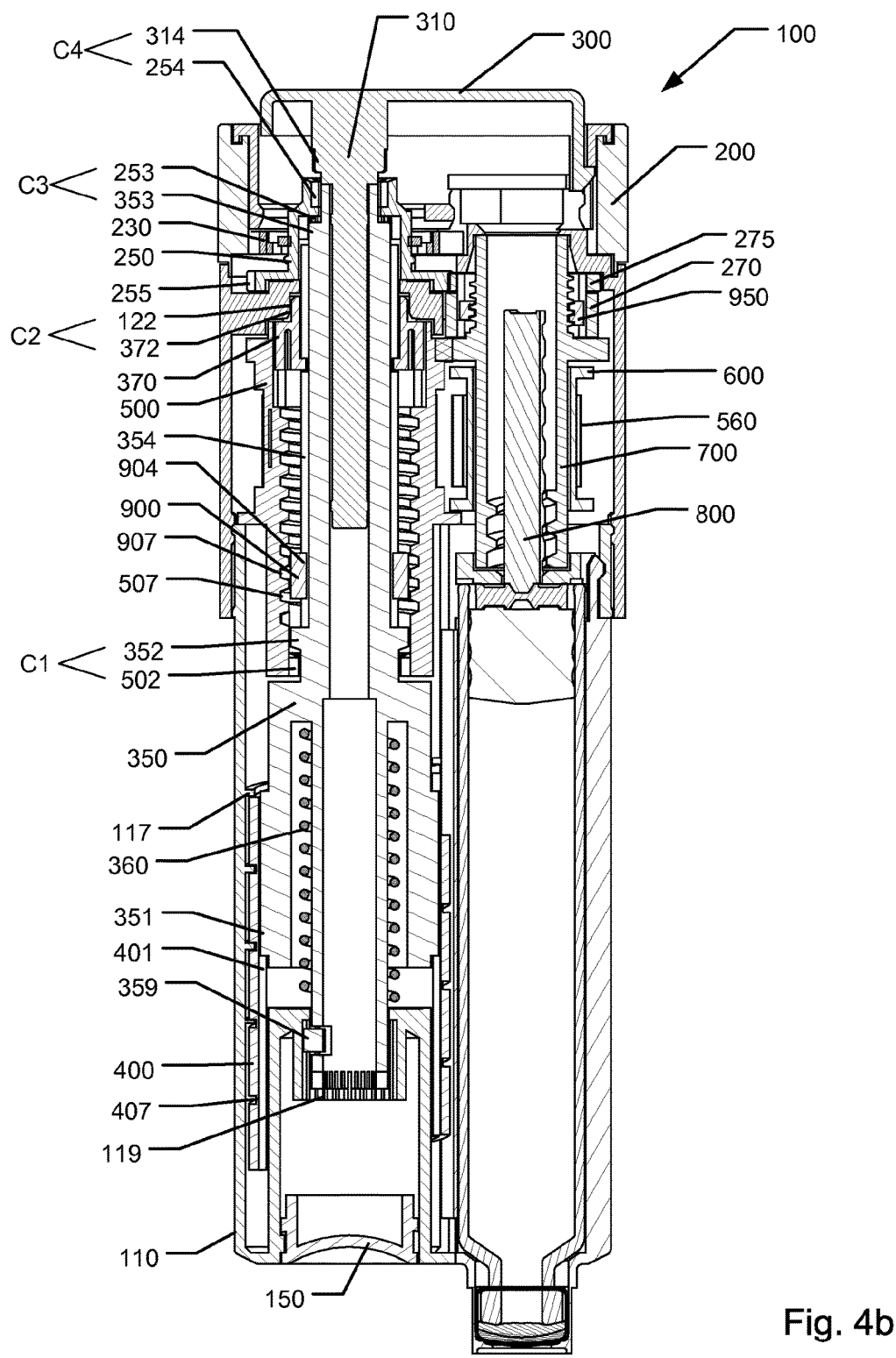
Figure 4C:
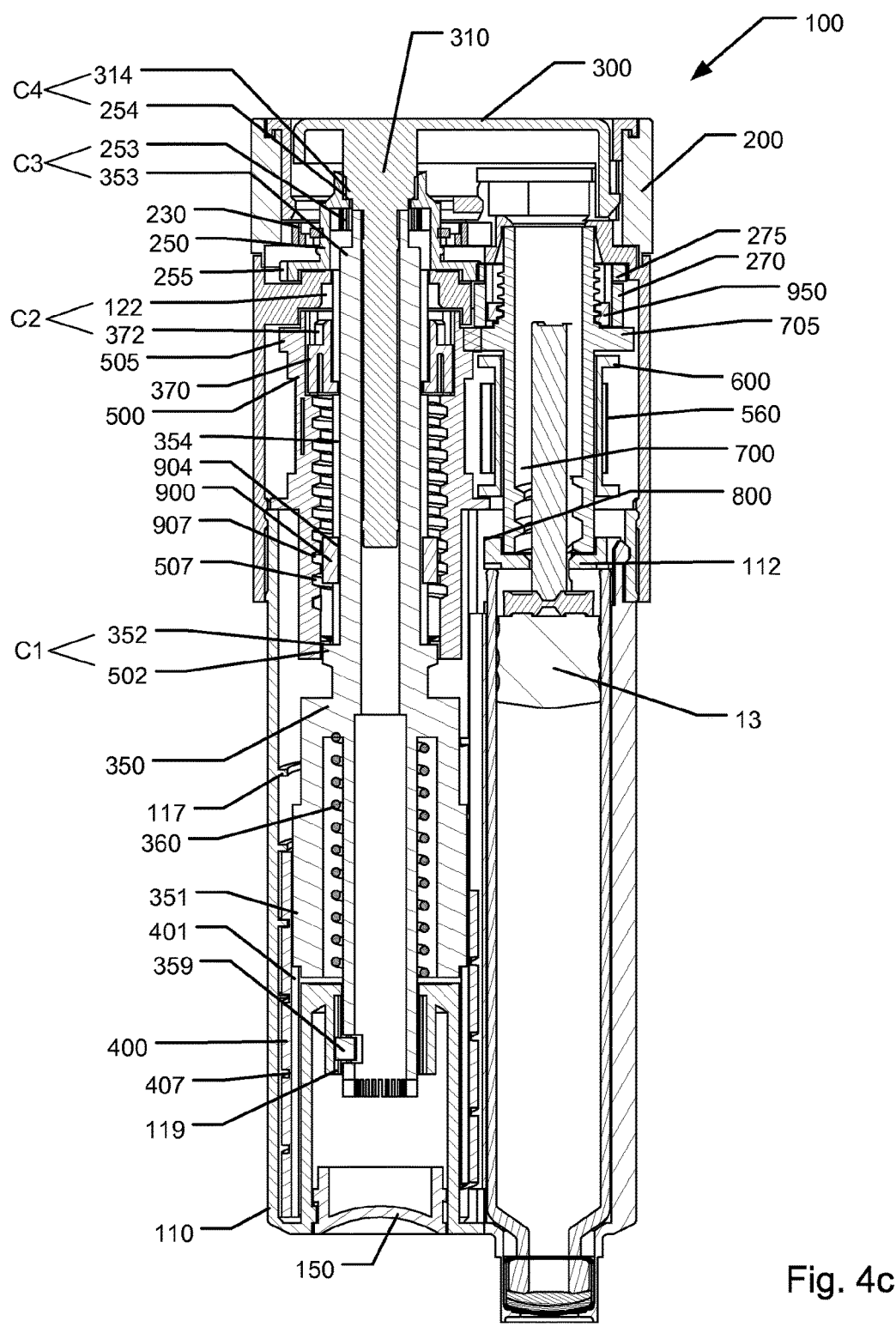
Figure 4D:
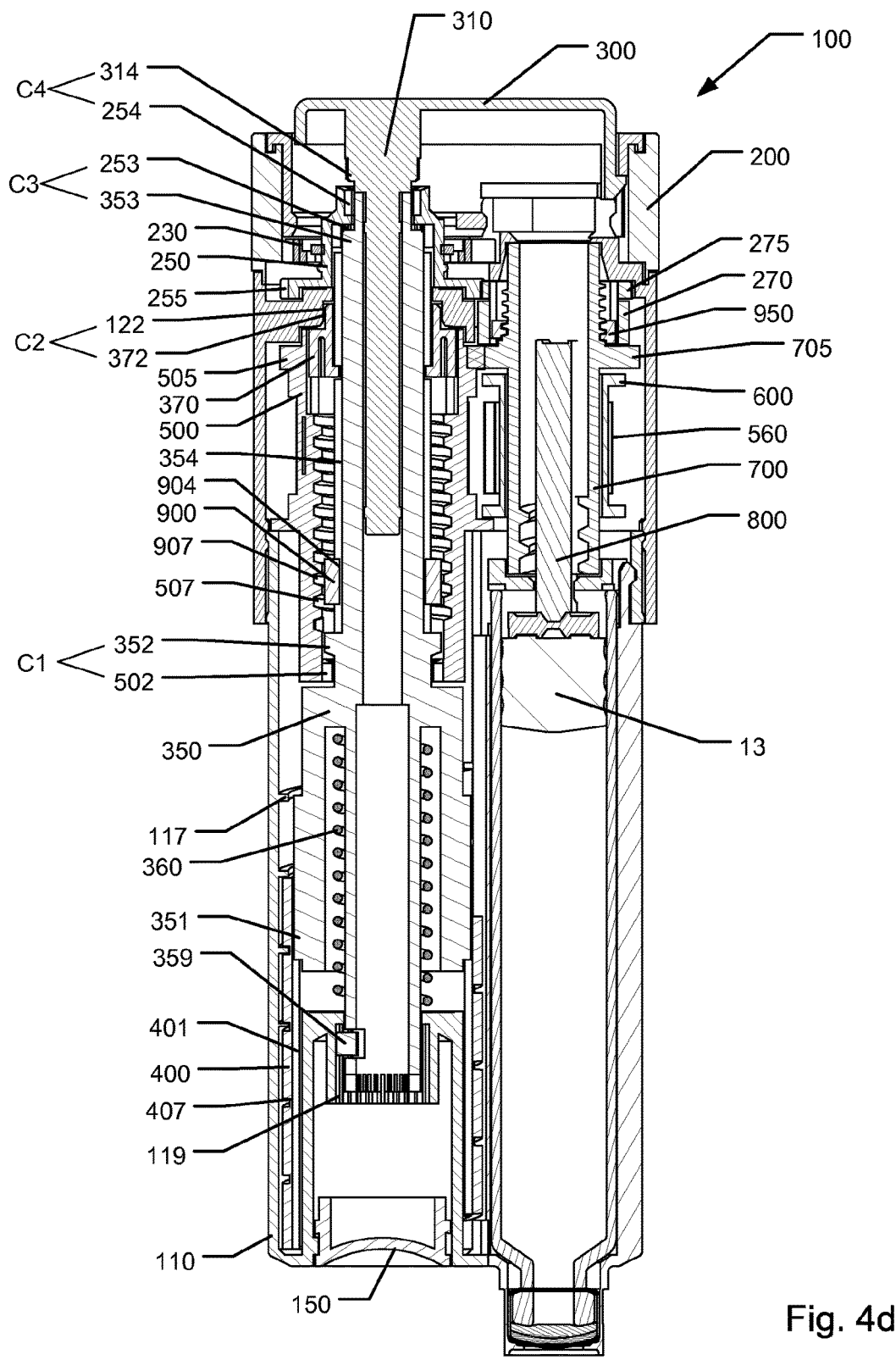

As noted above the FIG. 4a shows the device in an initial state before the setting of a dose, FIG. 4b shows the device in a state where the dosage selector 200 has been operated to set a particular size of a dose, FIG. 4c shows the device in a state where the injection button 300 has been pushed down and where the injection of the set dose has been completed and, finally, FIG. 4d shows the device in a state after completion of the injection of the set dose and where the injection button 300 has been released.

By comparing states shown in the FIGS. 4a, 4b, 4c and 4d, the movement of each of the clutch engagements C1, C2, C3 and C4 will become evident. Also, in accordance with the above description, the particular movements of the EOC mechanism and the secondary stop limiter providing the safety mechanism will become evident.

Turning now to FIG. 2b, the dose capturing unit 20 will be further described. The dose capturing unit 20 includes a body section 20k configured for cooperating with the distal housing part 110 to retain the dose capturing unit 20 relative to the injection device 100. An electronic display 20g is arranged at a distal portion of dose capturing unit 20 so that information provided on the display is visible through a transparent distal surface of the body section 20k. A circuit board 20f is arranged within the body section 20k and includes various electronic components such as a microcontroller 20i, one or more sensors, a battery 20h and various connectors for connecting further components arranged remotely from the circuit board.

A rotatable mass unit 20a is arranged to be rotatable around the dose setting axis, i.e. coaxially with dose control member 350 and configured to physically engage and lock rotationally relative to the dose control member 350. The rotatable mass unit 20a is made of a material having such a weight that the presence of the dose capturing unit 20 with the rotatable mass unit 20a limits the peak expelling speed experienced during a dose expelling procedure. In the shown embodiment, also a friction based brake pad 20j acts on the rotatable mass unit 20a to limit the rotational speed of the dose control member 350. Alternatively, the brake providing the counteracting force may be formed by suitably providing a frictional engagement with a shaft 20b discussed below. As noted above, other types of speed limiting mechanisms may be provided as an alternative or in addition to the ones shown in FIG. 2b.

A rotatable identifier 20c is connected by means of shaft 20b to the rotatable mass unit 20a. In the shown embodiment, the rotatable identifier 20c includes a multi-pole magnetic ring. In this embodiment a Hall element sensor 20d is arranged next to rotatable identifier 20c. Thus a magnetic linear encoder is provided decoding the rotation of the magnetic ring. As the magnetic ring follows rotation of the dose control member 350, the rotational positions or movements of the dose control member 350 can be captured by means of the magnetic linear encoder.

In the shown embodiment, a switch 20e is arranged to sense the axial position of the dose control member 350 and hence provides information as to whether the injection device is in dose setting mode or in dose expelling mode. The size of a dose is calculated based on the incremental angle measured while the dose control member 350 rotates while it remains in a current mode of operation. Hence, the electronics of the dose capturing unit is able to capture information relating both to positional information and/or movements occurring during dose setting but also during expelling of a set dose and is able to discriminate between data obtained in to the two operation modes of the injection device 100.

The electronic display 20g may be configured to display the current dose setting of the injection device and/or the amount of drug that has been expelled during the last expelling operation. The dose capturing unit 20 further includes a memory configured for holding dose size and related timing information for the last expelling action, and optionally a number of recent time-dose logs. The dose capturing unit may further be provided with an output port for wired or wireless upload of data to an external device, e.g. to the users smartphone or a doctors personal computer. Electronic display 20g may in some embodiments be omitted so that the dose capturing unit 20 only serves as an information storage that enables upload of the time-dose log to an external device.

The measuring principle of the dose capturing unit 20 may be provided by other suitable encoding technology adapted to capture rotational and/or axial information of the dose control member 350. Likewise, such encoding technology could be adapted to monitor movements of other components of the device such as the EOC track follower 900. Hence, the above described magnetic linear encoder may be substituted by other encoders using such as optics, galvanic contacts, induction, capacitive coupling or potentiometer type sensors. The rotary position encoder may be configured as a relative sensor or an absolute sensor. When the encoders use optical sensors or galvanic contacts, the identifier may be in the form of a Gray code pattern, either as a drum-shaped pattern arrange on a radially outwards facing or a radially inwards facing cylindrical surface or on a plane surface of a circular disk.

A rotatable identifier may be arranged in the dose capturing unit 20 as a component that belongs to the dose capturing unit 20 and wherein the rotatable identifier directly couples to the dose control member 350 (as shown in FIG. 2a). Alternatively the rotatable identifier couples to dose control member 350 via one or more gear-wheels. Other embodiments may include the rotatable identifier to be integrated into the injection device 100, such as integrated into or arranged onto dose control member 350 so that the dose sensor 20d of dose capturing unit 20 directly senses rotational information provided on the dose control member 350.

In other embodiments, the dosing member according to the invention may be defined by a component other than the dose control member 350 provided such component moves to an extent corresponding to the extent of movement of the piston rod 800 during the expelling of a set dose. As an example, the device shown in FIG. 2a may be modified to allow the rotary position of the drive member 500 to be captured by the dose capturing unit 20. As the drive member 500 only rotates during expelling of a set dose, the above switch 20e may be omitted as the rotation performed by drive member may be directly captured to obtain data relating to the amount of expelled doses. Such an embodiment provides for a particularly simple and inexpensive solution. However, in embodiments that are configured for capturing the rotational position of drive member 500, the axial position of the dose control member 350 may in some circumstances be utilized for waking up the rotational dose sensor upon the injection device being shifted from the dose setting mode to the dose expelling mode.

In the embodiment shown on the figures, the injection device defines a pre-filled injection device where a drug filled cartridge is arranged irremovably within the device. Subsequent to expelling the entire contents of the cartridge the pre-filled injection device is intended to be disposed of and, optionally, be replaced by a new disposable device. However, in other embodiments being slightly modified, the injection device may be adapted to be used as a device of the durable kind, wherein a first cartridge is replaced by a new one when the first cartridge has been emptied.

In line with the invention as set forth above, the invention is generally applicable to medical delivery devices, regardless of the kind of administration route for delivering a beneficial agent to the user. Also, the invention may be implemented in both manual injectors where the user directly delivers the necessary mechanical energy during the delivery process as well as spring assisted injectors where a pre-stressed or user strained spring in part or fully delivers the necessary mechanical energy during the delivery process. Further, the invention may be used in connection with other medical injection devices where actuators having other energy sources than spring actuators are used, such as pneumatically operated actuators having a pneumatic storage, prime mover actuators having an electrochemical cell storage or even electrical actuators having an electrical accumulator storage.

In the above description of the exemplary embodiments, the different structures providing the desired relations between the different components just as the means providing the described functionality for the different components have been described to a degree to which the concept of the present invention will be apparent to the skilled reader. The detailed construction and specification for the different structures are considered the object of a normal design procedure performed by the skilled person along the lines set out in the present specification.

The invention claimed is:

1. A medical injection system, comprising an injection device configured for setting and expelling a set dose amount of a drug from a reservoir, and an electronically controlled dose capturing unit configured for being attached relative to the injection device and for capturing data relating to expelling of drug from the injection device,
   wherein the injection device comprises:
      a housing,
      expelling structure for expelling an amount of drug from the reservoir, comprising:
         (i) a setting structure comprising a dosing member allowing a user to set a dose amount of drug to be expelled,
         (ii) an actuation structure for releasing the drug expelling structure to expel the set dose amount, and
         (iii) a mechanical energy storage unit coupled to the actuation structure which upon release exerts a driving force for driving the expelling structure to expel the set dose amount when the actuation structure is actuated, wherein the dosing member moves relative to another component of the injection device during expelling of the set dose amount, the extent of relative movement being indicative of the amount of drug being expelled, wherein the dose capturing unit comprises:

dose sensor adapted to sense said relative movement performed by the dosing member to capture data representing the extent of relative movement of the dosing member during expelling of the set dose amount, and a body that accommodates the dose sensor, and wherein the body of the dose capturing unit is releasably attachable relative to the injection device, and wherein the dose capturing unit when attached relative to the injection device couples to the expelling structure to exert a counteracting force to the force exerted by the mechanical energy storage unit to limit the speed of relative movement of the dosing member during expelling of the set dose amount.

2. The medical injection system as defined in claim 1, wherein the injection device is so configured that, when the dose capturing unit is not attached relative to the injection device, the injection device is operable allowing the user to set a dose amount to be expelled and to expel a set dose amount.

3. The medical injection system as defined in claim 1, wherein the dose capturing unit comprises a movable mass that couples to the expelling structure so that the movable mass is moved when the expelling structure is operated for providing the counteracting force.

4. The medical injection system as defined in claim 1, wherein the dose capturing unit couples to the expelling structure to provide a frictional force (F) for providing the counteracting force.

5. The medical injection system as defined in claim 1, wherein the dosing member of the injection device is a component that performs a rotating movement during expelling of a set dose amount.

6. The medical injection system as defined in claim 1, wherein the dose capturing unit, when attached to the injection device, defines a speed limiting mechanism for providing the counteracting force, the speed limiting mechanism incorporating one or more of the speed limiting mechanisms selected from the group consisting of a friction speed limiter, an inertia speed limiter, a fluidic speed limiter, an eddy current speed limiter and a centrifugal speed limiter.

7. The medical injection system as defined in claim 1, wherein the reservoir of the injection device is a cylindrical cartridge having a piston movable in a distal direction towards an expelling end of the cartridge, wherein a central longitudinal axis of the cartridge defines a first axis, wherein the dosing member is rotatable around a second axis that is spaced relative to the first axis, and wherein the dose capturing unit attaches to the injection device at a distal end of the housing of the device.

8. The medical injection system as defined in claim 1, wherein when the dose capturing unit is attached relative to the housing of the injection device the exterior housing defined by the combined apparatus defined by the injection device and the dose capturing unit includes a distal facing surface that is defined by a component of the dose capturing unit.

9. The medical injection system as defined in claim 1, wherein the dose capturing unit comprises one or more components that mechanically or magnetically engages with a component of the expelling structure when the dose capturing unit is attached to the injection device.

10. The medical injection system as defined in claim 9, wherein the dose capturing unit comprises one or more components that mechanically engages with the dosing member of the injection device when the dose capturing unit is attached to the injection device.

11. The medical injection system as defined in claim 1, wherein the mechanical energy storage unit is a spring device that is strained to accumulate energy and wherein the accumulated energy upon actuation of the actuation structure is released to drive the expelling structure to expel the set dose amount.

12. The medical injection system as defined in claim 11, wherein the dose setting structure comprises a movable dosage selector and wherein the spring device is strained when the dosage selector is operated to dial up a dose.

13. The medical injection system as defined in claim 11, wherein the mechanical energy storage unit comprises energy sufficient to drive the expelling structure for expelling the entire useable contents of the reservoir.

* * * * *

UNITED STATES PATENT AND TRADEMARK OFFICE
CERTIFICATE OF CORRECTION

PATENT NO.         : 10,117,999 B2
APPLICATION NO.    : 14/759558
DATED              : November 6, 2018
INVENTOR(S)        : Jens Christian Andersen Page 1 of 1

It is certified that error appears in the above-identified patent and that said Letters Patent is hereby corrected as shown below:

In the Claims

In Claim number 1, Column 23, Line number 9, please correct the below to read as follows:
"a dose sensor adapted to sense said relative movement..."

Signed and Sealed this
Ninth Day of April, 2019

Andrei Iancu
*Director of the United States Patent and Trademark Office*